(12) United States Patent
Hendrix et al.

(10) Patent No.: US 7,615,558 B2
(45) Date of Patent: Nov. 10, 2009

(54) 6-ARYLMETHYLPRAZOLO[3,4-D]PYRIMIDINES

(75) Inventors: Martin Hendrix, Odenthal (DE); Lars Bärfacker, Oberhausen (DE); Christina Erb, Kriftel (DE); Frank-Thorsten Hafner, Wuppertal (DE); Heike Heckroth, Wuppertal (DE); Dagmar Karthaus, Solingen (DE); Adrian Tersteegen, Wuppertal (DE); Franz-Josef van der Staay, Dronten (NL); Marja van Kampen, Düsseldorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 10/556,437

(22) PCT Filed: Apr. 27, 2004

(86) PCT No.: PCT/EP2004/004412

§ 371 (c)(1),
(2), (4) Date: Oct. 10, 2006

(87) PCT Pub. No.: WO2004/099210

PCT Pub. Date: Nov. 18, 2004

(65) Prior Publication Data

US 2007/0161662 A1 Jul. 12, 2007

(30) Foreign Application Priority Data

May 9, 2003 (DE) .................. 103 20 785

(51) Int. Cl.
C07D 487/04 (2006.01)
A61K 31/519 (2006.01)
A61P 25/28 (2006.01)

(52) U.S. Cl. ................... 514/262.1; 544/262

(58) Field of Classification Search ........... 544/262; 514/262.1
See application file for complete search history.

(56) References Cited

U.S. PATENT DOCUMENTS

| 3,165,520 | A | * | 1/1965 | Schmidt et al. ........... 544/262 |
| 3,732,225 | A | | 5/1973 | Breuer et al. |
| 5,002,949 | A | | 3/1991 | Peseckis et al. |
| 5,256,668 | A | | 10/1993 | Hsu et al. |
| 5,656,629 | A | | 8/1997 | Bacon et al. |
| 5,977,118 | A | | 11/1999 | Bacon et al. |
| 2004/0266736 | A1 | | 12/2004 | Wunder et al. |
| 2006/0100222 | A1 | | 5/2006 | Boss et al. |
| 2006/0106035 | A1 | | 5/2006 | Hendrix et al. |
| 2006/0111372 | A1 | | 5/2006 | Hendrix et al. |
| 2007/0105876 | A1 | | 5/2007 | Hendrix et al. |
| 2007/0161662 | A1 | | 7/2007 | Hendrix et al. |

FOREIGN PATENT DOCUMENTS

| CA | 2 283 211 A1 | 9/1998 |
| CA | 2 417 631 A1 | 1/2003 |
| CA | 2 484 997 A1 | 11/2003 |
| CA | 2 496 194 A1 | 3/2004 |
| CA | 2 496 292 A1 | 4/2004 |
| CA | 2 496 308 A1 | 4/2004 |
| CH | 396 923 | 8/1965 |
| CH | 396 924 | 8/1965 |
| CH | 396 925 | 8/1965 |
| CH | 396 926 | 8/1965 |
| CH | 396 927 | 8/1965 |
| DE | 1 147 234 | 4/1963 |
| DE | 1 149 013 | 5/1963 |
| DE | 1 153 023 | 8/1963 |
| DE | 1 156 415 | 10/1963 |
| DE | 2 408 906 | 2/1974 |
| DE | 101 56 249 A1 | 5/2003 |
| EP | 0 130 735 A1 | 1/1985 |
| EP | 0 995 751 A2 | 4/2000 |
| GB | 937726 | 9/1963 |
| GB | 973361 | 10/1964 |
| WO | 95/10506 A1 | 4/1995 |
| WO | 98/10765 A1 | 3/1998 |
| WO | 98/40384 A1 | 9/1998 |
| WO | 99/41253 A1 | 8/1999 |
| WO | 00/18758 A1 | 4/2000 |
| WO | 02/06288 A1 | 1/2002 |
| WO | 02/09713 A2 | 2/2002 |
| WO | WO 02/68423 A1 | 6/2002 |
| WO | WO 02/055082 A1 | 7/2002 |
| WO | 02/098864 A1 | 12/2002 |
| WO | 03/041725 A2 | 5/2003 |

(Continued)

OTHER PUBLICATIONS

Vipaagunta et. al. (Advanced Drug Delivery Reviews, 2001, (48), 3-26.*

(Continued)

*Primary Examiner*—James O Wilson
*Assistant Examiner*—Susanna Moore
(74) *Attorney, Agent, or Firm*—Michael P. Morris; Mary-Ellen M. Devlin; Edouard G. Lebel

(57) ABSTRACT

Described are 6-arylmethylpyrazolo[3,4-d]pyrimidines of the following formula:

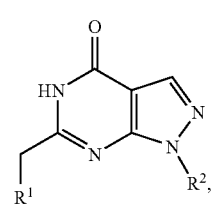

(I)

processes for their preparation and their use for producing medicaments for improving perception, concentration, learning and/or memory.

6 Claims, No Drawings

FOREIGN PATENT DOCUMENTS

| WO | WO 03/037899 A1 | 8/2003 |
|---|---|---|
| WO | 03/093269 A2 | 11/2003 |
| WO | WO 2004/026286 A1 | 1/2004 |
| WO | WO 2004/026876 A1 | 1/2004 |
| WO | WO 2004/018474 A1 | 4/2004 |

OTHER PUBLICATIONS

International Search Report for corresponding international application PCT/EP2004/004412 mailed Jul. 17, 2004.

International Search Report for PCT/EP2004/006477 mailed Oct. 27, 2004.

International Search Report for PCT/EP03/08923 mailed Dec. 15, 2003.

International Search Report for PCT/EP03/08979 mailed Nov. 25, 2003.

International Search Report for PCT/EP03/08880 mailed Apr. 16, 2004.

International Search Report for PCT/EP2004/004455 mailed Sep. 17, 2004.

International Search Report for PCT/EP2004/014872 mailed May 19, 2005.

Ji-Ye Wei, et al; Molecular and Pharmacological Analysis of Cyclic Nucleotide-Gated Channel Function in the Central Nervous System, Progress in Neurobiology (1998) vol. 56, pp. 37-64.

Douglas A. Fisher, et al; Isolation and Characterization of PDE8A, A Novel Human cGMP-specific Phosphodiesterase; Journal of Biological Chemistry (1998) vol. 273, No. 25, pp. 15559-1 5564.

Michel Guipponi, et al; Identification and Characterization of a Novel Cydic Nudeotide Phosphodiesterase Gene (PDE8A) That Maps to 21q22.3: Alternative Splicing of mRNA Transcripts, Genomic Structure and Sequence; Hum Genet (1998) vol. 103, pp. 386-392.

Scott H. Sonderling, et al; Identification and Characterization of a Novel Family of Cyclic Nucleotide Phosphodiesterases, Journal of Biological Chemistry (1998) vol. 273, No. 25. pp. 15553-15558.

Svetlana G. Andreeva, et al; Expression of cGMP-Specific Phosphodiesterase 9A mRNA in the Rat Brain, Journal of Neuroscience (2001) vol. 21, No. 22, pp. 9068-9076.

Timothy J. Martins, et al; Purification and Characterization of a Cydic GMP-stimulated Cyclic Nucledide Phosphodiesterase from Bovine Tissues, Journal of Biological Chemistry (1982) vol. 257, No. 4, pp. 1973-1979.

Sharron H. Francis, et al; Characterization of a Novel cGMP Binding Protein from Rat Lung, Journal of Biological Chemistry (1980) vol. 255, No. 2, pp. 620-626.

Peter G. Gillespie, et al; Characterization of a Bovine Cone Photoreceptor Phosphodiesterase Purified by Cydic GMP-Sepharose Chromatography; Journal of Biological Chemistry (1988) vol. 263. No. 17, pp. 8133-8141.

Lindsay Fawcett, et al; Molecular Cloning and Characterization of a Distinct Human Phosphodiesterase Gene Family: PDE11A; Proc. Natl. Acad. *Sci.* (2000) vol. 97, No. 7, pp. 3702-3707.

Seiko Murashima, et al; Characterization of Particulate Cyclic Nucleotide Phosphodiesterases from Bovine Brain: Purification of a Distinct cGMP-Stimulated Isoenzyme; Biochemistry (1990) vol. 29, No. 22 pp. 5285-5292.

Scott H. Sonderling, et al; Regulation of CAMP and cGMP signaling: new phosphodiesterases and new functions; Current Opinion in Cell Biology (2000) vol. 12, pp. 174-179.

Akira Miyashita, et al; Studies on Pyrazolo[3,4-d]Pyrimidine Derivatives. XVIII. Facile Preparation of 1H-Pyrazolo[3,4-d]Pyrimidin-4(5H)-Ones; Heterocycles (1990) vol. 31, No. 7, p. 1309-1314.

Kate Loughney, et al; Isolation and Characterization of cDNAs Corresponding to Two Human Calcium, Calmodulin-regulated. 3',5'-Cyclic Nucleotide Phosphodiesterases, Journal of Biological Chemistry (1996) vol. 271. No. 2, pp. 796-806.

Guy J. Rosman, et al; Isolation and Characterization of Human cDNAs encoding a cGMPstimulated 3',5'-Cyclic Nucleotide Phosphodiesterase; Gene (1997) vol. 191, pp. 89-95.

Takashi Miki, et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.

Rena Obernolte, et al; The cDNA of a Human Lymphocyte cyclic-AMP Phosphodiesterase (PDE IV) Reveals a Multigene Family; Gene (1993) vol. 129, pp. 239-247.

Kate Loughney, et al; Isolation and Characterization of cDNAs encoding PDE5A, a Human cGMP-Binding, cGMP-Speafic Y.9-Cydic Nudeotide Phosphodiesterase; Gene (1998) vol. 216, pp. 139-147.

J. M. Hetman, et al; Cloning and Characterization of PDE7B, a CAMP-specific Phosphodiesterase, Proc. Natl. Acad. Sci. (2000) vol. 97, No. 1, pp. 472-476.

Douglas A. Fisher, et al; Isolation and Characterization of PDEM, a Novel Human CAMP-Specific Phosphodiesterase; Biochemical and Biophysical Research Communications (1998) vol. 246, pp. 570-577.

Kotomi Fujishige, et al; Cloning and Characterization of a Novel Human Phosphodiesterase That Hydrolyzes R21 Both CAMP and cGMP (PDE10A); Journal of Biological Chemistry (1999) vol. 274, No. 26, pp. 18438-.18445.

James E. Huettner, et al; Primary Culture of Identified Neurons from the Visual Cortex of Postnatal Rats; Journal of Neuroscience (1986) vol. 6, pp. 3044-3060.

Magnus Roenn, et al; Palladium (II)-Catalyzed Cyclization Using Molecular Oxygen as Reoxidant; Tetrahedron Letters (1995) vol. 36, No. 42, pp. 7749-7752.

C. C. Cheng, et al; Potential Purine Antagonists VII. Synthesis of 6-Alkylpyrazolo-[3,4-d]pyrimidines; Journal of Organic Chemistry (1958) vol. 23 pp. 191-200.

Hieke Gielen, et al; A Novel Approach to Amidines from Esters; Tetrahedron Letters (2002) vol. 43 pp. 419-421.

K. Hemender Reddy, et al; Versatile Synthesis of 6-Alkyl/Aryl-1H-Pyrazolo[3,4-d]Pyrimidin-4[5H]-Ones; Indian Journal of Chemistry (1992) vol. 31B, pp. 163-166.

Arne Schousboe, et al; Role of Ca++ and Other Second Messengers in Excitatory Amino Acid Receptor Mediated Neuogeneration: Clinical Perspective; Clinical Neuroscience (1997) vol. 4, pp. 194-198.

Accessed on Mar. 18, 2007. http://mentalhealth.org.uk/information/mental-health-a-z/dementia/.

Sudha R. Vippagunta, et al; Crystalline Solids; Advanced Drug Delivery Reviews (2001) vol. 48 pp. 3-26.

Anthony R. West; Solid Solutions; John Wiley & Sons, chapter 10 pp. 358 and 365 (1988).

Joachim Ulrich; Crystallization: 4. Crystal Characteristics; Kirk-Othmer Encyclopedia of Chemical Technology; Aug. 2002.

Claire Lugnier; Cyclic Nucleotide Phosphodiesterase (PDE) Superfamily: A New Target for the Development of Specific Therapeutic Agents; Pharmacology & Therapeutics (2006) vol. 109 pp. 366-398.

Jehan Bagli, et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

Rudolf Gompper, et al; Substituted Dithiocarboxylic Acids and Ketene Thioacetals; Institute for Organic Chemistry Technology (1962) vol. 95, pp. 2861-2870. German & English Translation.

P. Schmidt, et al; A New Synthesis of Pyrazolo[3,4-d]Pyrimidines Having Coronary Dilation Properties; Helvetica Chimica Acta (1962) vol. XLV, No. 189, pp. 1620-1627. German & English Translation.

F. Josef van der Staay, et al., "The novel selective PDE9 inhibitor BAY 73-6691 improves learning and memory in rodents", Neuropharmacology, 55 (2008) pp. 908-916.

U. Ebert, et al., "Scopolamine model of dementia: electroencephalogram findings and cognitive performance", European Journal of Clinical Investigation, (1998) 28, pp. 944-949.

Jos Prickaerts, et al., "Possible role of nitric oxide-cyclic GMP pathway in object recognition memory: Effect of 7-nitroindazole and zaprinast", European Journal of Pharmacology 337 (1997) pp. 125-136.

F. Zaragoza Dörwald, "Side Reactions in Organic Synthesis", A Guide to Successful Systhesis Design, 2005, 4 pages.

Kenneth F. Podraza, "Reductive Cyclization of Ketoesters Utilizing Sodium Cyanoborohydride: Synthesis of γ- and δ-Lactones" J. Heterocyclic Chem., 24, 193 (1987).

Internet Article, "Amnesia", From Wikipedia, the free encyclopedia, 3 pages, downloaded, Dec. 18, 2008.

Reid IA, "Role of phosphodiesterase isoenzymes in the control of rennin secretion: effects of selective enzyme inhibitors", Curr Pharm Des, Sep. 1999; 5(9); 725-35, abstract.

Edwin J. Weeber, et al., "Molecular Genetics of Human Cognition", Molecular Inventions, vol. 2, Issue 6, Oct. 2002, pp. 376-391.

* cited by examiner

6-ARYLMETHYLPRAZOLO[3,4-D]PYRIMIDINES

This application is a 371 of PCT/E2004/004412, filed Apr. 27, 2004.

The invention relates to novel 6-arylmethyl-substituted pyrazolopyrimidines, process for their preparation and their use for producing medicaments for improving perception, concentration, learning and/or memory.

Inhibition of phosphordiesterases modulates the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56: 37-64). The phosphodiesterases (PDE) are a control mechanism for controlling the activity of cAMP and cGMP and thus in turn these physiological processes. PDEs hydrolyse the cyclic monophosphates to the inactive monophosphates AMP and GMP. At least 21 PDE genes have now been described (*Exp. Opin. Investig. Drugs* 2000, 9, 1354-3784). These 21 PDE genes can be divided on the basis of their sequence homology into 11 PDE families (for proposed nomenclature, see http://depts.washington.edu/pde/Nomenclature.html.). Individual PDE genes within a family are differentiated by letters (e.g. PDE1A and PDE1B). If different splice variants within a gene also occur, this is then indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nM, PDE9A has high affinity for cGMP. In addition, PDE9A is selective for cGMP (Km for cAMP=230 µM). PDE9A has no cGMP binding domain, suggesting allosteric enzyme regulation by cGMP. It was shown in a Western blot analysis that PDE9A is expressed in humans inter alia in testes, brain, small intestine, skeletal muscle, heart, lung, thymus and spleen. The highest expression was found in the brain, small intestine, heart and spleen (Fisher et al., *J. Biol. Chem.*, 1998, 273 (25): 15559-15564). The gene for human PDE9A is located on chromosome 21q22.3 and comprises 21 exons. To date, 4 alternative splice variants of PDE9A have been identified (Guipponi et al., *Hum. Genet.*, 1998, 103: 386-392). Classical PDE inhibitors do not inhibit human PDE9A. Thus, IBMX, dipyridamole, SKF94120, rolipram and vinpocetine show no inhibition on the isolated enzyme in concentrations of up to 100 µM. An $IC_{50}$ of 35 µM has been demonstrated for zaprinast (Fisher et al., *J. Biol. Chem.*, 1998, 273 (25): 15559-15564).

Murine PDE9A was cloned and sequenced in 1998 by Soderling et al. (*J. Biol. Chem.*, 1998, 273 (19): 15553-15558). This has, like the human form, high affinity for cGMP with a Km of 70 nM. Particularly high expression was found in the mouse kidney, brain, lung and heart. Murine PDE9A is not inhibited by IBMX in concentrations below 200 µM either; the $IC_{50}$ for zaprinast is 29 µM (Soderling et al., *J. Biol. Chem.*, 1998, 273 (19): 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22): 9068-9076). The hippocampus, cortex and basal forebrain in particular play an important role in learning and memory processes.

As already mentioned above, PDE9A is distinguished by having particularly high affinity for cGMP. PDE9A is therefore active even at low physiological concentrations, in contrast to PDE2A (Km=10 µM; Martins et al., *J. Biol. Chem.*, 1982, 257: 1973-1979), PDE5A (Km=4 µM; Francis et al., *J. Biol. Chem.*, 1980, 255: 620-626), PDE6A (Km=17 µM; Gillespie and Beavo, *J. Biol. Chem.*, 1988, 263 (17): 8133-8141) and PDE11A (Km=0.52 µM; Fawcett et al., *Proc. Nat. Acad. Sci.*, 2000, 97 (7): 3702-3707). In contrast to PDE2A (Murashima et al., *Biochemistry*, 1990, 29: 5285-5292), the catalytic activity of PDE9A is not increased by cGMP because it has no GAF domain (cGMP-binding domain via which the PDE activity is allosterically increased) (Beavo et al., *Current Opinion in Cell Biology*, 2000, 12: 174-179). PDE9A inhibitors may therefore lead to an increase in the baseline cGMP concentration.

WO 98/40384 discloses pyrazoleopyrimidines which are PDE1, 2 and 5 inhibitors and can be employed for the treatment of cardiovascular and cerebrovascular disorders and disorders of the urogenital system.

CH 396 924, CH 396 925, CH 396 926, CH 396 927, DE 1 147 234, DE 1 149 013, GB 937,726 describe pyrazoleopyrimidines which have a coronary-dilating effect and which can be employed for the treatment of disturbances of myocardial blood flow.

U.S. Pat. No. 3,732,225 describes pyrazoleopyrimidines which have an antiinflammatory and blood glucose-lowering effect.

DE 2 408 906 describes styrylpyrazoleopyrimidines which can be employed as antimicrobial and antiinflammatory agents for the treatment of, for example, oedema.

The present invention relates to compounds of the formula

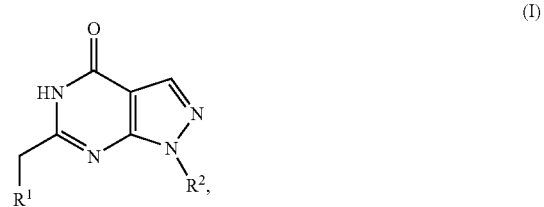

(I)

in which
$R^1$ is phenyl, pyridyl or thiophenyl which are optionally substituted by up to 3 substituents independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroaryl-carbonylamino, $C_1$-$C_6$-alkylsulphonylamino, $C_1$-$C_6$-alkylsulphonyl, $C_1$-$C_6$-alkylthio,
where $C_1$-$C_6$-alkyl, $C_1$-$C_6$-alkoxy, $C_1$-$C_6$-alkylamino, $C_6$-$C_{10}$-arylcarbonylamino, $C_1$C_6$alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by a radical selected from the group of hydroxy, cyano, halogen, hydroxycarbonyl and a group of the formula —$NR^3R^4$, where $R^3$ and $R^4$ are independently of one another hydrogen or $C_1$-$C_6$-alkyl, or $R^3$ and $R^4$ together with the nitrogen atom to which they are bonded are 5- to 8-membered heterocyclyl, $R^2$ is phenyl or heteroaryl, where phenyl is substituted by 1 to 3 radicals and heteroaryl is optionally substituted by 1 to 3 radicals in each case independently of one another selected from the group of $C_1$-$C_6$-alkyl, $C_1$-$C_6$-alkoxy, hydroxycarbonyl, cyano, trifluoromethyl, amino, nitro, hydroxy, $C_1$-$C_6$-alkylamino, halogen, $C_6$-$C_{10}$-arylcarbonylamino, $C_1$-$C_6$-alkyl-carbonylamino, $C_1$-$C_6$-alkylaminocarbonyl, $C_1$-$C_6$-alkoxycarbonyl, $C_6$-$C_{10}$-arylamino-carbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio, where $C_1$-$C_6$-alkyl, $C_1$-$C_6$-alkoxy, $C_1$-$C_6$-alkylamino, $C_6$-$C_{10}$-arylcarbonylamino, $C_1$-$C_6$-alkylcarbonylamino, $C_1$-$C_6$-alkylaminocarbonyl, $C_1$-$C_6$-alkoxycarbonyl, $C_6$-$C_{10}$-arylaminocarbonyl, heteroarylaminocarbonyl, heteroarylcarbonylamino, $C_1$-$C_6$-alkylsulphonylamino, $C_1$-$C_6$-alkylsulphonyl and $C_1$-$C_6$-alkylthio are optionally substituted by a radical selected from the group of hydroxy, cyano, halogen, hydroxycarbonyl and a group of the formula —$NR^3R^4$, where $R^3$ and $R^4$ have the meanings indicated above, and the salts, solvates and/or solvates of the salts thereof.

The compounds of the invention may, depending on their structure, exist in stereoisomeric forms (enantiomers, diastereomers). The invention therefore relates to the enantiomers or diastereomers and respective mixtures thereof. The sterically pure constituents can be isolated in a known manner from such mixtures of enantiomers and/or diastereomers.

Salts which are preferred for these purposes of the invention are physiologically acceptable salts of the compounds of the invention.

Physiologically acceptable salts of the compounds (I) include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dehydroabietylamine, arginine, lysine, ethylenediamine and methylpiperidine.

Solvates refers for the purposes of the invention to those forms of the compounds which form, in the solid or liquid state, a complex by coordination with solvent molecules. Hydrates are a specific form of solvates in which the coordination takes place with water.

For the purposes of the present invention, the substituents have the following meaning, unless specified otherwise:

$C_1$-$C_6$-Alkoxy is a straight-chain or branched alkoxy radical having 1 to 6, preferably 1 to 4, particularly preferably having 1 to 3 carbon atoms. Preferred examples include methoxy, ethoxy, n-propoxy, isopropoxy, tert-butoxy, n-pentoxy and n-hexoxy.

$C_1$-$C_6$-Alkyl is a straight-chain or branched alkyl radical having 1 to 6, preferably 1 to 4, particularly preferably 1 to 3, carbon atoms. Preferred examples include methyl, ethyl, n-propyl, isopropyl, tert-butyl, n-pentyl and n-hexyl.

Halogen is fluorine, chlorine, bromine and iodine. Fluorine, chlorine, bromine are preferred, and fluorine and chlorine are particularly preferred.

$C_1$-$C_6$-Alkylamino is a straight-chain or branched mono- or dialkylamino radical having 1 to 6, preferably 1 to 4 and particularly preferably having 1 to 3 carbon atoms. Preferred examples include methylamino, ethylamino, n-propylamino, isopropylamino, tert-butylamino, n-pentylamino and n-hexylamino, dimethylamino, diethylamino, di-n-propylamino, diisopropylamino, di-t-butylamino, di-n-pentylamino, di-n-hexylamino, ethylmethylamino, isopropylmethylamino, n-butylethylamino and n-hexyl-i-pentylamino.

$C_1$-$C_6$-Alkylcarbonylamino is an alkylcarbonyl radical linked via an amino group, where the alkyl radical may be straight-chain or branched and comprises 1 to 6, preferably 1 to 4 and particularly preferably 1 to 3, carbon atoms. Preferred examples include methylcarbonylamino, ethylcarbonylamino, n-propylcarbonylamino, isopropylcarbonylamino, tert-butylcarbonylamino, n-pentylcarbonylamino and n-hexylcarbonylamino.

$C_1$-$C_6$-Alkylaminocarbonyl is a mono- or dialkylamino radical linked via a carbonyl group, where the alkyl radicals may be identical or different, are straight-chain or branched and each comprise 1 to 6, preferably 1 to 4 and particularly preferably 1 to 3, carbon atoms. Preferred examples include methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, dimethylaminocarbonyl, diethylaminocarbonyl, di-n-propylaminocarbonyl, diisopropylaminocarbonyl, di-t-butylamino-carbonyl, di-n-pentylaminocarbonyl, di-n-hexylaminocarbonyl, ethylmethylaminocarbonyl, isopropylmethylaminocarbonyl, n-butylethylaminocarbonyl and n-hexyl-i-pentylaminocarbonyl. A further possibility in the case of a dialkylamino radical is for the two alkyl radicals to form together with the nitrogen atom to which they are bonded a 5- to 8-membered heterocyclyl.

$C_6$-$C_{10}$-Arylaminocarbonyl is an arylamino radical linked via a carbonyl group. Preferred examples include phenylaminocarbonyl and naphthylaminocarbonyl.

$C_6$-$C_{10}$-Arylcarbonylamino is an arylcarbonyl radical linked via an amino group. Preferred examples include phenylcarbonylamino and naphthylcarbonylamino.

$C_1$-$C_6$-Alkylsulphonylamino is a straight-chain or branched alkylsulphonylamino radical having 1 to 6, preferably 1 to 4 and particularly preferably having 1 to 3, carbon atoms. Preferred examples include methylsulphonylamino, ethylsulphonylamino, n-propylsulphonylamino, isopropylsulphonylamino, tert-butylsulphonylamino, n-pentylsulphonylamino and n-hexylsulphonylamino.

$C_1$-$C_6$-Alkylsulphonyl is a straight-chain or branched alkylsulphonyl radical having 1 to 6, preferably 1 to 4 and particularly preferably having 1 to 3, carbon atoms. Preferred examples include methylsulphonyl, ethylsulphonyl, n-propylsulphonyl, isopropylsulphonyl, tert-butylsulphonyl, n-pentylsulphonyl and n-hexylsulphonyl.

$C_1$-$C_6$-Alkylthio is a straight-chain or branched alkylthio radical having 1 to 6, preferably 1 to 4 and particularly preferably having 1 to 3, carbon atoms. Preferred examples include methylthio, ethylthio, n-propylthio, isopropylthio, tert-butylthio, n-pentylthio and n-hexylthio.

Heteroaryl is an aromatic, mono- or bicyclic radical having 5 to 10 ring atoms and up to 5 heteroatoms from the series S, O and/or N. 5- to 6-membered heteroaryls having up to 4 heteroatoms are preferred. The heteroaryl radical may be bonded via a carbon or nitrogen atom. Preferred examples include thienyl, furyl, pyrrolyl, thiazolyl, oxazolyl, imidazolyl, tetrazolyl, pyridyl, pyrimidinyl, pyridazinyl, indolyl, indazolyl, benzofuranyl, benzothiophenyl, quinolinyl and isoquinolinyl.

Heteroarylaminocarbonyl is a heteroarylamino radical linked via a carbonyl group. Preferred examples include thienylaminocarbonyl, furylaminocarbonyl, pyrrolylaminocarbonyl, thiazolylaminocarbonyl, oxazolylaminocarbonyl, imidazolylaminocarbonyl, tetrazolylaminocarbonyl, pyridylaminocarbonyl, pyrimidinylaminocarbonyl, pyridazinylaminocarbonyl, indolylaminocarbonyl, indazolylaminocarbonyl, benzofuranylaminocarbonyl, benzothiophenylaminocarbonyl, quinolinylaminocarbonyl and isoquinolinylaminocarbonyl.

Heteroarylcarbonylamino is a heteroarylcarbonyl radical linked via an amino group. Preferred examples include thienylcarbonylamino, furylcarbonylamino, pyrrolylcarbonylamino, thiazolylcarbonylamino, oxazolylcarbonylamino, imidazolylcarbonylamino, tetrazolylcarbonylamino, pyridylcarbonylamino, pyrimidinylcarbonylamino, pyridazinylcarbonylamino, indolylcarbonylamino, indazolylcarbonylamino, benzofuranylcarbonylamino, benzothiophenylcarbonylamino, quinolinylcarbonylamino and isoquinolinylcarbonylamino.

5- to 8-membered heterocyclyl is a mono- or polycyclic heterocyclic radical having 5 to 8 ring atoms and up to 3, preferably 2, heteroatoms or hetero groups from the series N, O, S, SO, $SO_2$. Mono- or bicyclic heterocyclyl is preferred. Monocyclic heterocyclyl is particularly preferred. N and O are preferred as heteroatoms. The heterocyclyl radicals may be saturated or partially unsaturated. Saturated heterocyclyl radicals are preferred. 5- to 7-membered heterocyclyl radicals are particularly preferred. Preferred examples include oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl.

6-membered heteroaryl is an aromatic radical having 6 ring atoms and up to 2 nitrogen atoms. The heteroaryl radical is bonded via a carbon atom. Preferred examples include pyridyl, pyrimidinyl, pyridazinyl and pyrazinyl.

When radicals in the compounds of the invention are optionally substituted, unless otherwise specified substitution by up to three identical or different substituents is preferred.

The compounds of the invention may also be in the form of tautomers as shown by way of example below:

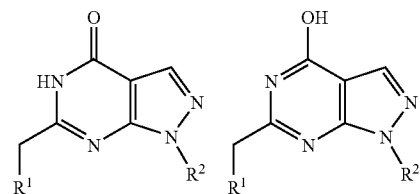

A further embodiment of the invention relates to compounds of the formula (1)
in which
$R^1$ is phenyl, pyridyl or thiophenyl, which are optionally substituted by up to 3 radicals independently of one another selected from the group of $C_1$-$C_4$-alkyl, $C_1$-$C_4$-alkoxy, hydroxycarbonyl, cyano, trifluoromethyl, amino, hydroxy, $C_1$-$C_4$-alkylamino, fluorine, chlorine, bromine, $C_6$-$C_{10}$-arylcarbonylamino, $C_1$-$C_4$-alkylcarbonylamino, $C_1$-$C_4$-alkylaminocarbonyl, $C_1$-$C_4$-alkoxycarbonyl, $C_6$-$C_{10}$-arylaminocarbonyl, heteroarylaminocarbonyl, heteroarylcarbonylamino, $C_1$-$C_4$-alkylsulphonylamino, $C_1$-$C_4$-alkylsulphonyl, $C_1$-$C_4$-alkylthio,
where $C_1$-$C_4$-alkyl and $C_1$-$C_4$-alkoxy are optionally substituted by a radical selected from the group of hydroxy, cyano, fluorine, chlorine, bromine, hydroxycarbonyl and a group of the formula —$NR^3R^4$,
where
$R^3$ and $R^4$ are independently hydrogen or $C_1$-$C_4$-alkyl, or
$R^3$ and $R^4$ together with the nitrogen atom to which they are bonded are 5 - to 6-membered heterocyclyl,
$R^2$ is phenyl, pyrimidyl or pyridyl, where phenyl is substituted by 1 to 3 radicals and pyrimidyl and pyridyl are optionally substituted by 1 to 3 radicals in each case independently of one another selected from the group of $C_1$-$C_4$-alkyl, $C_1$-$C_4$-alkoxy, hydroxycarbonyl, cyano, trifluoromethyl, amino, hydroxy, $C_1$-$C_4$-alkylamino, fluorine, chlorine, bromine, $C_6$-$C_{10}$-arylcarbonylamino, $C_1$-$C_4$-alkylcarbonylamino, $C_1$-$C_4$-alkylaminocarbonyl, $C_1$-$C_4$-alkoxycarbonyl, $C_6$-$C_{10}$-arylaminocarbonyl, heteroarylaminocarbonyl, heteroarylcarbonylamino, $C_1$-$C_4$-alkylsulphonylamino, $C_1$-$C_4$-alkylsulphonyl, $C_1$-$C_4$-alkylthio,
where $C_1$-$C_4$-alkyl and $C_1$-$C_4$-alkoxy are optionally substituted by a radical selected from the group of hydroxy, cyano, fluorine, chlorine, bromine, hydroxycarbonyl and a group of the formula —$NR^3R^4$,
where $R^3$ and $R^4$ have the meanings indicated above, and the salts, solvates and/or solvates of the salts thereof.

A further embodiment of the invention relates to compounds of the formula (I)
in which $R^1$ has the meanings indicated above, and
$R^2$ is phenyl or pyridyl, where phenyl is substituted by 1 to 2 radicals and pyridyl is optionally substituted by 1 to 2 radicals in each case independently of one another selected from the group of methyl, ethyl, 2-propyl, trifluoromethyl, methoxy, ethoxy, fluorine and chlorine, and the salts, solvates and/or solvates of the salts thereof.

A further embodiment of the invention relates to compounds of the formula (I), in which
$R^1$ is phenyl, pyridyl or thiophenyl, which are optionally substituted by up to 2 radicals independently of one another selected from the group of $C_1$-$C_4$-alkyl, fluorine, chlorine, trifluoromethyl, hydroxy, phenylcarbonylamino, $C_1$-$C_4$-alkylcarbonylamino, $C_1$-$C_4$-alkylaminocarbonyl or phenylaminocarbonyl, $R^2$ is phenyl or pyridyl, where phenyl is substituted by 1 to 2 radicals and pyridyl is optionally substituted by 1 to 2 radicals in each case independently of one another selected from the group of methyl, ethyl, 2-propyl, trifluoromethyl, methoxy, ethoxy, fluorine and chlorine, and the salts, solvates and/or solvates of the salts thereof.

A process for preparing compounds of the invention of the formula (I) has also been found, characterized in that either

[A] compounds of the formula

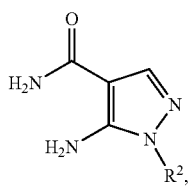

(II)

in which
$R^2$ has the meanings indicated above,
are converted by reaction with a compound of the formula $R^1$—$CH_2$—C(O)-Z (IIIa), in which
$R^1$ has the meanings indicated above,
and
Z is chlorine or bromine,
in an inert solvent and in the presence of a base, initially into compounds of the formula

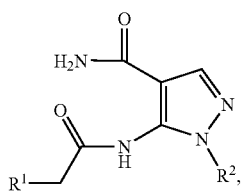

(IV)

in which
$R^1$ and $R^2$ have the meanings indicated above,
and then cyclized in an inert solvent in the presence of a base to compounds of the formula (I), or

[B] compounds of the formula (II) are reacted with a compound of the formula $R^1$—$CH_2$—C(O)—$OR^3$ (IIIb), in which
$R^1$ has the meanings indicated above,
and
$R^3$ is methyl or ethyl,
in an inert solvent and in the presence of a base, with direct cyclization to (I), or

[C] compounds of the formula

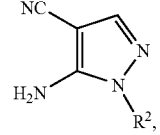

(V)

in which
$R^2$ has the meanings indicated above,
are converted initially by reaction with a compound of the formula (IIIa) in an inert solvent and in the presence of a base into compounds of the formula

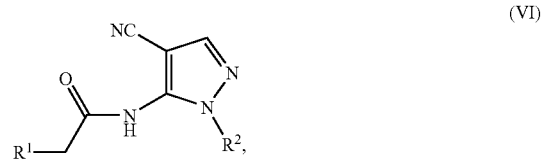

(VI)

in which
$R^1$ and $R^2$ have the meanings indicated above,
and the latter are cyclized in a second step in an inert solvent and in the presence of a base and of an oxidizing agent to (I), and the resulting compounds of the formula (I) are where appropriate reacted with the appropriate (i) solvents and/or (ii) bases or acids to give their solvates, salts and/or solvates of the salts.

Suitable for the first step of process [A] and of process [C] are inert organic solvents which are not changed under the reaction conditions. These preferably include ethers such as, for example, diethyl ether, dioxane, tetrahydrofuran or glycol dimethyl ether, or toluene or pyridine. It is likewise possible to employ mixtures of the solvents mentioned. Tetrahydrofuran, toluene or pyridine are particularly preferred.

Generally suitable bases are alkali metal hydrides such as, for example, sodium hydride, or cyclic amines such as, for example, piperidine, pyridine, dimethylaminopyridine (DMAP) or $C_1$-$C_4$-alkylamines such as, for example, triethylamine. Sodium hydride, pyridine and/or dimethylaminopyridine are preferred.

The base is generally employed in an amount of from 1 mol to 4 mol, preferably from 1.2 mol to 3 mol, in each case based on 1 mol of the compounds of the formula (II) or (V).

In one variant, the reaction is carried out in pyridine to which a catalytic amount of DMAP is added. It is also possible where appropriate to add toluene.

The reaction temperature can generally be varied within a relatively wide range. It is generally in a range from −20° C. to +200° C., preferably from 0° C. to +100° C.

Solvents suitable for the cyclization in the second step of processes [A] and [C] are the usual organic solvents. These preferably include alcohols such as methanol, ethanol, propanol, isopropanol, n-butanol or tert-butanol, or ethers such as tetrahydrofuran or dioxane, or dimethylformamide or dimethyl sulphoxide. Alcohols such as methanol, ethanol, propanol, isopropanol or tert-butanol are particularly preferably used. It is likewise possible to employ mixtures of the solvents mentioned.

Bases suitable for the cyclization in the second step of processes [A] and [C] are the usual inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium bicarbonate, or alkali metal alcoholates such as sodium methanolate, sodium ethanolate, potassium methanolate, potassium ethanolate or potassium tert-butanolate. Potassium carbonate, sodium hydroxide and potassium tert-butanolate are particularly preferred.

When carrying out the cyclization, the base is generally employed in an amount of from 2 mol to 6 mol, preferably from 3 mol to 5 mol, in each case based on 1 mol of the compounds of the formula (IV) or (VI).

Oxidizing agents suitable for the cyclization in the second step of process [C] are, for example, hydrogen peroxide or sodium borate. Hydrogen peroxide is preferred.

The cyclization in processes [A], [B] and [C] is generally carried out in a temperature range from 0° C. to +160° C., preferably at the boiling point of the particular solvent.

The cyclization is generally carried out under atmospheric pressure. However, it is also possible to carry out the process under elevated pressure or under reduced pressure (e.g. in a range from 0.5 to 5 bar).

Solvents suitable for process [B] are the alcohols mentioned above for the second step of processes [A] and [C], with preference for ethanol.

Bases suitable for process [B] are alkali metal hydrides such as, for example, sodium or potassium hydride, or alkali metal alcoholates such as, for example, sodium methanolate, ethanolate, isopropoxide or potassium tert-butoxide. Sodium hydride is preferred.

The base is employed in an amount of from 2 mol to 8 mol, preferably from 3 mol to 6 mol, in each case based on 1 mol of the compounds of the formula (II).

The compounds of the formula (II) are known or can be prepared for example by initially condensing ethoxymethyl-enemalonoxnitrile with hydrazine derivatives of the formula $$R^2—NH—NH_2 \quad (VII),$$

in which $R^2$ has the meanings indicated above, in an inert solvent to give pyrazolecarbonitriles of the formula (V), and then reacting the latter with one of the oxidizing agents mentioned above, preferably hydrogen peroxide, in the presence of ammonia [cf., for example, A. Miyashita et al., Heterocycles 1990, 31, 1309ff].

The compounds of the formulae (IIIa), (IIIb) and (VII) are commercially available, known from the literature or can be prepared in analogy to processes known from the literature.

The process of the invention can be illustrated by way of example by the following formula scheme:

Scheme

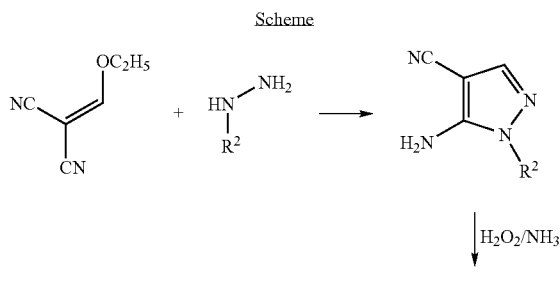

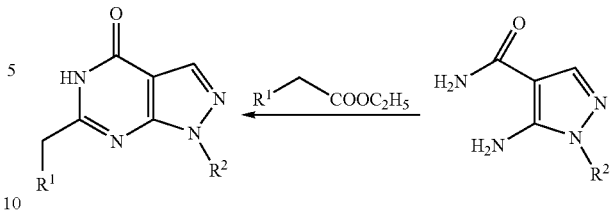

Further processes for preparing pyrazoleo[3,4-d]pyrimidin-4-ones are known and can likewise be employed for synthesizing the compounds of the invention (see, for example: P. Schmidt et al., *Helvetica Chimica Acta* 1962, 189, 1620ff.).

The compounds of the invention show a valuable range of pharmacological effects which could not have been predicted. They are distinguished in particular by inhibition of PDE9A.

It has surprisingly been found that the compounds of the invention are suitable for producing medicaments for improving perception, concentration, learning or memory.

The compounds of the invention can, by reason of their pharmacological properties, be employed alone or in combination with other medicaments for improving perception, concentration, learning and/or memory.

The compounds of the invention are particularly suitable for improving perception, concentration, learning or memory after cognitive impairments like those occurring in particular in situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

The in vitro effect of the compounds of the invention can be shown with the following biological assays:

PDE Inhibition

Recombinant PDE1C (GenBank/EMBL Accession Number: NM_005020, Loughney et al. *J. Biol. Chem.* 1996 271, 796-806), PDE2A (GenBank/EMBL Accession Number: NM_002599, Rosman et al. *Gene* 1997 191, 89-95), PDE3B (GenBank/EMBL Accession Number: NM_000922, Miki et al. *Genomics* 1996, 36, 476-485), PDE4B (GenBank/EMBL Accession Number: NM_002600, Obernolte et al. *Gene*. 1993, 129, 239-247), PDE5A (GenBank/EMBL Accession Number: NM_001083, Loughney et al. *Gene* 1998, 216, 139-147), PDE7B (GenBank/EMBL Accession Number: NM_018945, Hetman et al. *Proc. Natl. Acad. Sci. U.S.A.* 2000, 97, 472476), PDE8A (GenBank/EMBL Accession Number: AF_056490, Fisher et al. *Biochem. Biophys. Res. Commun.* 1998 246, 570-577), PDE9A (Fisher et al., *J. Biol. Chem,* 1998, 273 (25): 15559-15564), E10A (GenBank/EMBL Accession Number: NM_06661, Fujishige et al. *J. Biol Chem.* 1999, 274, 18438-45), PDE11A (GenBank/EMBL Accession Number: NM_016953, Fawcett et al. *Proc. Natl. Acad. Sci.* 2000, 97, 3702-3707) were expressed in Sf9 cells with the aid of the pFASTBAC baculovirus expression system (GibcoBRL).

The test substances are dissolved in 100% DMSO and serially diluted to determine their in vitro effect on PDE 9A. Typically, serial dilutions from 200 µM to 1.6 µM are prepared (resulting final concentrations in the assay: 4 µM to 0.032 µM). 2 µL portions of the diluted substance solutions are introduced into the wells of microtiter plates (Isoplate; Wallac Inc., Atlanta, Ga.). Then 50 µL of a dilution of the PDE9A preparation described above are added. The dilution of the PDE9A preparation is chosen so that less than 70% of the substrate is converted during the subsequent incubation (typical dilution: 1:10000; dilution buffer: 50 mM Tris/HCl pH 7.5, 8.3 mM $MgCl_2$, 1.7 mM EDTA, 0.2% BSA). The substrate, [8-$^3$H] guanosine 3',5'-cyclic phosphate (1 µCi/µL; Amersham Pharmacia Biotech., Piscataway, N.J.) is diluted 1:2000 with assay buffer (50 mM Tris/HCl pH 7.5, 8.3 mM $MgCl_2$, 1.7 mM EDTA) to a concentration of 0.0005 µCi/µL. The enzyme reaction is finally started by adding 50 µL (0.025 µCi) of the diluted substrate. The assay mixtures are incubated at room temperature for 60 min and the reaction is stopped by adding 25 µl of a PDE9A inhibitor (e.g. the inhibitor from preparation example 1, final concentration 10 µM) dissolved in assay buffer. Immediately thereafter, 25 µL of a suspension containing 18 mg/mL Yttrium Scintillation Proximity Beads (Amersham Pharmacia Biotech., Piscataway, N.J.) are added. The microtiter plates are sealed with a film and left to stand at room temperature for 60 min. The plates are then measured for 30 s per well in a Microbeta scintillation counter (Wallac Inc., Atlanta, Ga.). $IC_{50}$ values are determined from the graphical plot of the substance concentration versus the percentage inhibition.

Representative examples of the inhibiting effect of the compounds of the invention on PDE9A are listed by means of the $IC_{50}$ values in Table 1:

TABLE 1

| Example | $IC_{50}$ [nM] |
| --- | --- |
| 2 | 50 |
| 4 | 64 |
| 9 | <30 |
| 21 | <30 |

The in vitro effect of test substances on recombinant PDE3B, PDE4B, PDE7B, PDE8A, PDE10A and PDE11A is determined in accordance with the assay protocol described above for PDE 9A with the following adaptations: [5',8-$^3$H] adenosine 3',5'-cyclic phosphate (1 µCi/µL; Amersham Pharmacia Biotech., Piscataway, N.J.) is used as substrate. Addition of an inhibitor solution to stop the reaction is unnecessary. Instead, the incubation of substrate and PDE is followed immediately by addition of the yttrium scintillation proximity beads as described above and thus the reaction is stopped. To determine a corresponding effect on recombinant PDE1C, PDE2A and PDE5A, the protocol is additionally adapted as follows: with PDE1C, additionally $10^{-7}$ M calmodulin and 3 mM $CaCl_2$ are added to the reaction mixture. PDE2A is stimulated in the assay by adding 1 µM cGMP and is assayed with a BSA concentration of 0.01%. The substrate employed for PDE1C and PDE2A is [5',8-$^3$H] adenosine 3',5'-cyclic phosphate (1 µCi/µL; Amersham Pharmacia Biotech., Piscataway, N.J.), and for PDE5A is [8-$^3$H] guanosine 3',5'-cyclic phosphate (1 µCi/µL; Amersham Pharmacia Biotech., Piscataway, N.J.).

Long-Term Potentiation

Long-term potentiation is regarded as a cellular correlate of learning and memory processes. The following method can be used to determine whether PDE 9 inhibition has an influence on long-term potentiation:

Rat hippocampi are placed at an angle of about 70 degrees to the cutting blade (chopper). 400 µm-thick slices of the hippocampus are prepared. The slices are removed from the blade using a very soft, thoroughly wetted brush (marten hair) and transferred into a glass vessel with cold nutrient solution (124 mM NaCl, 4.9 mM KCl, 1.3 mM $MgSO_4$*7 $H_2O$, 2.5 mM $CaCl^{2+}$ anhydrous, 1.2 mM $KH_2PO_4$, 25.6 mM $NaHCO_3$, 10 mM glucose, pH 7.4) gassed with 95% $O_2$/5% $CO_2$. During the measurement, the slices are kept in a temperature-controlled chamber under a 1-3 mm-high liquid level. The flow rate is 2.5 ml/min. The preliminary gassing takes place under a slightly elevated pressure (about 1 atm) and through a microneedle in the prechamber. The slice chamber is connected to the prechamber in such a way that a minicirculation can be maintained. The minicirculation is driven by the 95% $O_2$/5% $CO_2$ flowing out through the microneedle. The freshly prepared hippocampus slices are adapted in the slice chamber at 33° C. for at least 1 hour.

The stimulus level is chosen so that the focal excitatory postsynaptic potentials (fEPSP) are 30% of the maximum excitatory postsynaptic potential (EPSP). A monopolar stimulation electrode consisting of lacquered stainless steel, and a constant-current biphasic stimulus generator (AM Systems 2100) are used for local stimulation of the Schaffer collaterals (voltage: 1 -5 V, pulse width of one polarity 0.1 ms, total pulse 0.2 ms). Glass electrodes (borosilicate glass with filament, 1-5 MOhm, diameter: 1.5 mm, tip diameter: 3-20 µm), filled with normal nutrient solution, are used to record the excitatory postsynaptic potentials (fEPSP) from the stratum radiatum. The field potentials are measured versus a chlorinated silver reference electrode located at the edge of the slice chamber using a DC voltage amplifier. The field potentials are filtered through a low-pass filter (5 kHz). The slope of the fEPSPs (fEPSP slope) is determined for the statistical analysis of the experiments. The recording, analysis and control of the experiment takes place with the aid of a software program (PWIN) which was developed in the Department of Neurophysiology. The formation of the average fEPSP slopes at the respective time points and construction of the diagrams takes place with the aid of the EXCEL software, with automatic data recording by an appropriate macro.

Superfusion of the hippocampus slices with a 10 µM solution of the compounds of the invention leads to a significant increase in the LTP.

The in vivo effect of the compounds of the invention can be shown for example as follows:

Social Recognition Test

The social recognition test is a learning and memory test. It measures the ability of rats to distinguish between known and unknown members of the same species. This test is therefore suitable for examining the learning- or memory-improving effect of the substances of the invention.

Adult rats housed in groups are placed singly in test cages 30 min before the start of the test. Four min before the start of the test, the test animal is put in an observation box. After this adaptation time, a juvenile animal is put in with the test animal and the absolute time for which the adult animal inspects the young one is measured for 2 min (trial 1). All behaviours clearly directed at the young animal are measured, i.e. anogenital inspection, pursuit and grooming, during which the old animal was no further than 1 cm from the young animal. The juvenile is then removed, and the adult is treated with a compound of the invention or vehicle and subsequently returned to its own cage. The test is repeated after a retention time of 24 hours (trial 2). A diminished social interaction time compared with trial 1 indicates that the adult rat remembers the young animal.

The adult animals receive intraperitoneal injections either at a fixed time interval (e.g. 1 hour) before trial 1 or directly following trial 1 either with vehicle (10% ethanol, 20% Solutol, 70% physiological saline) or 0.1 mg/kg, 0.3 mg/kg, 1.0 mg/kg or 3.0 mg/kg compound of the invention dissolved in 10% ethanol, 20% Solutol, 70% physiological saline. Vehicle-treated rats show no reduction in the social interaction time in trial 2 compared with trial 1. They have consequently forgotten that they have already had contact with the young animal. Surprisingly, the social inter-action time in the second run after treatment with the compounds of the invention is significantly reduced compared with those treated with vehicle. This means that the substance-treated rats have remembered the juvenile animal and thus the compounds of the invention display an improving effect on learning and memory.

The novel active ingredients can be converted in a known manner into conventional formulations such as tablets, coated tablets, pills, granules, aerosols, syrups, emulsions, suspensions and solutions, using inert, nontoxic, pharmaceutically suitable excipients or solvents. In these cases, the therapeutically active compound should in each case be present in a concentration of about 0.5 to 90% by weight of the formulation, i.e. in amounts which are sufficient to reach the stated dose range.

The formulations are produced for example by extending the active ingredients with solvents and/or excipients, where appropriate with use of emulsifiers and/or dispersants, it being possible for example when water is used as diluent where appropriate to use organic solvents as auxiliary solvents.

Administration can take place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behaviour towards the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Unless indicated otherwise, all quantitative data relate to percentages by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

Abbreviations:

| | |
|---|---|
| DCI | direct chemical ionization (in MS) |
| DMSO | dimethyl sulphoxide |
| ESI | electrospray ionization (in MS) |
| Fp. | melting point |
| h | hour(s) |
| HPLC | high pressure, high performance liquid chromatography |
| LC-MS | coupled liquid chromatography-mass spectroscopy |
| min | minutes |
| MS | mass spectroscopy |
| NMR | nuclear magnetic resonance spectroscopy |
| $R_t$ | retention time (in HPLC) |
| TLC | thin-layer chromatography |

LC-MS Methods:

Method 1

Instrument: Micromass Platform LCZ with HPLC Agilent Series 1100; column: Grom-Sil 120 ODS-4 HE, 50 mm×2.0 mm, 3 µm; eluent A: 1 l of water+1 ml of 50% strength formic acid, eluent B: 1 l of acetonitrile+1 ml of 50% formic acid; gradient: 0.0 min 100% A→0.2 min 100% A→2.9 min 30%→3.1 min 10%→4.5 min 10% A; oven: 55° C; flow rate: 0.8 ml/min; UV detection: 208-400 nm.

Method 2

Instrument: Micromass Quattro LCZ, with IPLC Agilent Series 1100; column: Grom-Sil 120 ODS-4 HE, 50 mm×2.0 mm, 3 µm; eluent A: 1 l water+1 ml 50% strength formic acid, eluent B: 1 l acetonitrile+1 ml 50% strength formic acid; gradient: 0.0 min 100% A→0.2 min 100%→2.9 min 30% A→3.1 min 10% A→4.5 min 10% A; oven: 55° C; flow rate: 0.8 ml/min; UV detection: 208-400 nm.

Method 3

MS apparatus type: Micromass ZQ; HPLC apparatus type: Waters Alliance 2790; column: Grom-Sil 120 ODS-4 HE, 50×2 mm, 3.0 µm; eluent B: acetonitrile+0.05% formic acid, eluent A: water+0.05% formic acid; gradient: 0.0 min 5% B→2.0 min 40% B→4.5 min 90% B -5.5 min 90% B; oven: 45° C.; flow rate: 0.0 min 0.75 ml/min→4.5 min 0.75 ml/min→5.5 min 1.25 ml/min; UV detection: 210 nrm.

Method 4

MS apparatus type: Micromass TOF (LCT); HPLC apparatus type: 2-column switching, Waters 2690; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25% A→1.9 min 10% A→3.2 min 10% A; oven: 40° C.; flow rate: 3.0 ml/min; UV detection: 210 nm.

Method 5

MS apparatus type: Micromass ZQ; HPLC apparatus type: Waters Alliance 2790; column: Grom-Sil 120 ODS-4 HE 50 mm×2 mm, 3.0 µm; eluent B: acetonitrile+500 µl of 50% formic acid/l, eluent A: water+500 µl of 50% formic acid/l; gradient: 0.0 min 0% B→0.2 min 0% B→2.9 min 70% B→3.1 min 90% B→4.5 min 90% B; oven: 50° C; flow rate: 0.8 ml/min; UV detection: 210 nm.

Method 6

MS apparatus type: Micromass ZQ; HPLC apparatus type: TSP P4000, TSP AS300, TSP UV3000; column: Grom-Sil 120 ODS-4 HE, 50 mm×2 mm, 3.0 Jm; eluent A: water+250 µl of 50% strength formic acid/l, eluent B: acetonitrile+250 µl of 50% strength formic acid/l; gradient: 0.0 min 0%

B→0.2 min 0% B→2.9 min 70% B→3.1 min 90% B→4.5 min 90% B; oven: 50° C.; flow rate: 0.8 ml/min; UV detection: 210 nm.

Starting Compounds:

EXAMPLE 1A

5-Amino-1-(2,6-dimethylphenyl)-1H-pyrazole-4-carbonitrile

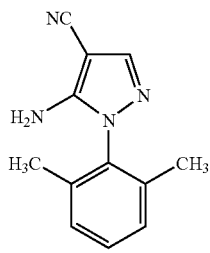

3.0 g (17.3 mmol) of 2,6-dimethylphenylhydrazine hydrochloride are suspended with 2.1 g (17.3 mmol) of ethoxymethylenemalononitrile in 40 ml of ethanol, and 7.3 ml (52.1 mmol) of triethylamine are added. The reaction mixture is heated to reflux for 3 h, during which a clear solution forms. After cooling to room temperature, diethyl ether is added to this. The triethyl-ammonium chloride which precipitates is filtered off. The solvent is removed in vacuo, and the residue is purified by preparative HPLC (YMC gel ODS-AQ S 5/15 μm; eluent A: water, eluent B: acetonitrile; gradient: 0 min 30% B, 5 min 30% B, 50 min 95% B). 2.3 g (62% of theory) of the product are obtained as yellow crystals.

LC-MS (Method 6): $R_t$=2.77 min. MS (ESI pos): m/z=213 (M+H)$^+$.

EXAMPLE 2A

5-Amino-1-(2,3-dimethylphenyl)-1H-pyrazole-4-carbonitrile

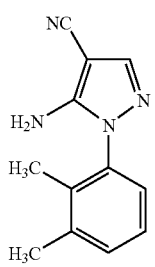

In analogy to the preparation of Example 1A, 2.08 g (56% of theory) of the desired product are obtained starting from 3 g (17.4 mmol) of 2,3-dimethylphenylhydrazine hydrochloride, 2.1 g (17.4 mmol) of ethoxymethylenemalononitrile and 7.3 ml (52.1 mmol) of triethylamine.

LC-MS (Method 6): $R_t$=2.79 min. MS (ESI pos): m/z=213 (M+H)$^+$.

EXAMPLE 3A

5-Amino-1-(4-methylphenyl)-1H-pyrazole-4-carbonitrile

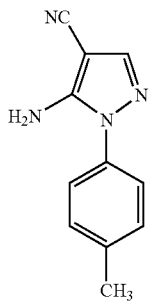

In analogy to the preparation of Example 1A, 2.16 g (57% of theory) of the desired product are obtained starting from 3 g (18.9 mmol) of 4-methylphenylhydrazine hydrochloride, 2.3 g (18.9 mmol) of ethoxymethylenemalononitrile and 7.9 ml (56.7 mmol) of triethylamine.

LC-MS (Method 1): $R_t$=3.0 min. MS (ESI pos): m/z=199 (M+H)$^+$.

EXAMPLE 4A

5-Amino-1-(2,6-dichlorophenyl)-1H-pyrazole-4-carbonitrile

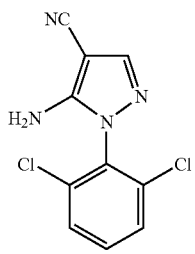

In analogy to the preparation of Example 1A, 2.9 g (83% of theory) of the desired product are obtained starting from 3 g (14.1 mmol) of 2,6-dichlorophenylhydrazine hydrochloride, 1.7 g (14.1 mmol) of ethoxymethylenemalononitrile and 5.8 ml (42.2 mmol) of triethylamine after purification by column chromatography (mobile phase dichloromethane/methanol 98:2).

LC-MS (Method 3): $R_t$=2.8 min. MS (ESI pos): m/z=253 (M+H)$^+$ $^1$H-NMR (300 MHz, DMSO-$d_6$): δ=6.82 (s, 2H), 7.59 (m, 2H), 7.69 (m, 1H), 7.80 (s, 1H) ppm.

EXAMPLE 5A

5-Amino-1-(2,5-dichlorophenyl)-1H-pyrazole-4-carbonitrile

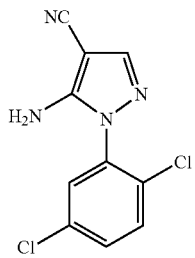

In analogy to the preparation of Example 1A, 2.2 g (51% of theory) of the desired product are obtained starting from 3 g (16.9 mmol) of 2,5-dichlorophenylhydrazine, 2.0 g (16.9 mmol) of ethoxymethylenemalononitrile and 7.1 ml (50.8 mmol) of triethylamine.

LC-MS (Method 1): $R_t$=3.2 min. MS (ESI pos): m/z=253 (M+H)$^+$.

EXAMPLE 6A

5-Amino-1-(2-nitrophenyl)-1H-pyrazole-4-carbonitrile

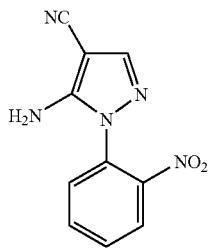

In analogy to the preparation of Example 1A, 1.9 g (53% of theory) of the desired product are obtained starting from 3 g (15.8 mmol) of 2-nitrophenylhydrazine hydrochloride, 1.93 g (16.9 mmol) of ethoxymethylenemalononitrile and 6.6 ml (47.6 mmol) of triethylamine.

LC-MS (Method 1): $R_t$=2.80 min. MS (ESI pos): m/z=230 (M+H)$^{+1}$H-NMR (300 MHz, DMSO-d$_6$): δ=6.87 (s, 2H), 7.72 (mn, 1H), 7.77 (s, 1H), 7.78 (m,1H), 7.88 (m, 1H), 8.16 (dd, 1H) ppm.

EXAMPLE 7A

5-Amino-1-(3-fluorophenyl)-1H-pyrazole-4-carbonitrile

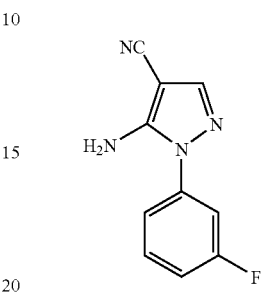

In analogy to the preparation of Example 1A, 1.5 g (31% of theory) of the desired product are obtained starting from 4 g (24.6 mmol) of 3-fluorophenylhydrazine hydrochloride, 3 g (24.6 mmol) of ethoxymethylenemalononitrile and 10.3 ml (73.8 mmol) of triethylamine.

LC-MS (Method 1): $R_t$=2.90 min. MS (ESI pos): m/z=203 (M+H)$^{+1}$H-NMR (300 MHz, DMSO-d$_6$): δ=6.81 (s, 2H), 7.28 (m, 1H), 7.36 (m, 2H), 7.57 (m, 1H), 7.80 (s, 1H) ppm.

EXAMPLE 8A

5-Amino-1-(3-chloropyridin-2-yl)-1H-pyrazole-4-carbonitrile

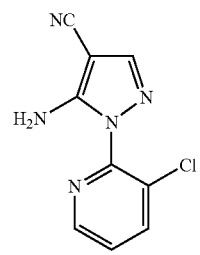

In analogy to the preparation of Example 1A, 0.4 g (53% of theory) of the desired product are obtained starting from 0.6 g (4.17 mmol) of 3-chloro-2-pyridylhydrazine, 0.51 g (4.17 mmol) of ethoxymethylenemalononitrile and 1.1 ml (8.3 mmol) of triethylamine and after purification by column chromatography (mobile phase dichloromethane/methanol 98:2).

LC-MS (Method 6): $R_t$=2.17 min. MS (ESI pos): m/z=220 (M+H)$^{+1}$H-NMR (300 MHz, DMSO-d$_6$): δ=6.87 (s, 2H), 7.63 (dd, 1H), 7.79 (s, 1H), 8.22 (dd, 1H), 8.54 (dd, 1H) ppm.

EXAMPLE 9A

5-Amino-1-(2-methylphenyl)-1H-pyrazole-4-carbonitrile

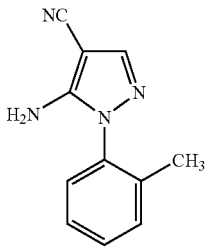

10.2 g (64.4 mmol) of 2-methylphenylhydrazine hydrochloride are suspended with 7.8 g (64.4 mmol) of ethoxymethylenemalononitrile in 100 ml of methanol, and 26.9 ml (193.3 mmol) of triethylamine are added. The reaction mixture is heated to reflux overnight, during which a clear solution forms. The solution is subsequently distilled off under reduced pressure, and the crude product is purified by column chromatography (silica gel, mobile phase dichloromethane). 10.8 g (85% of theory) of the desired product are obtained.

LC-MS (Method 1): $R_t$=3.10 min. MS (ESI pos): m/z=199 $(M+H)^+$.

EXAMPLE 10A

5-Amino-1-(2-ethylphenyl)-1H-pyrazole-4-carbonitrile

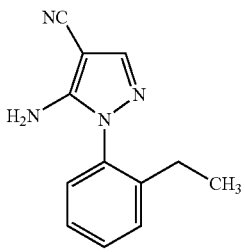

A solution of 3.0 g (17.0 mmol) of 2-ethylphenylhydrazine hydrochloride and 2.12 g (17.0 mmol) of ethoxymethylenemalononitrile in 36 ml of ethanol is mixed with 7.1 ml (51.1 mmol) of triethylamine and heated at 60° C. until the reaction is complete according to a TLC check (about 30 min). For working up, the solvent is stripped off, and the residue is taken up in dichloromethane, washed with saturated sodium bicarbonate solution and dried over sodium sulphate. Concentration results in a crude product which is purified by column chromatography on silica gel (mobile phase dichloromethane with 0-10% methanol). 3.05 g (83.5% of theory) of the desired product are obtained.

m.p.: 130° C. MS (ESI pos): m/z=213 $(M+H)^{+1}$H-NMR (300 MHz, DMSO-$d_6$): δ=1.0 (t, 3H), 2.35 (q, 2H), 6.4 (s, 2H), 7.2-7.5 (m, 4H), 7.7 (s, 1H) ppm.

EXAMPLE 11A

5-Amino-1-(2-trifluoromethylphenyl)-1H-pyrazole-4-carbonitrile

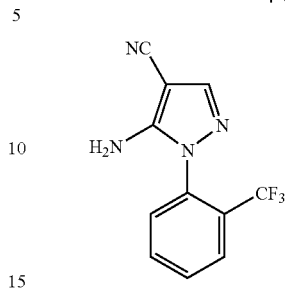

In analogy to the preparation of Example 10A, 5.02 g (76.9% of theory) of the desired product are obtained starting from 4.8 g (25.9 mmol) of 2-trifluoromethylphenylhydrazine hydrochloride, 3.16 g (25.9 mmol) of ethoxymethylenemalononitrile and 7.2 ml (51.7 mmol) of triethylamine.

m.p.: 190° C. MS (ESI pos): m/z=253 $(M+H)^{+1}$H-NMR (300 MHz, DMSO-$d_6$): δ=6.6 (s, 2H), 7.5 (d, 1H), 7.7-8.0 (m, 4H) ppm.

EXAMPLE 12A

5-Amino-1-(2-fluorophenyl)-1H-pyrazole-4-carbonitrile

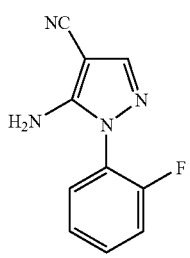

In analogy to the preparation of Example 10A, 5.13 g (88% purity, 84% of theory) of the desired product are obtained starting from 5.0 g (30.8 mmol) of 2-fluorophenylhydrazine hydrochloride, 3.27 g (26.7 mmol) of ethoxymethylenemalononitrile and 11.3 ml (81.3 mmol) of triethylamine.

MS (ESI pos): m/z=203 $(M+H)^{+1}$H-NMR (300 MHz, DMSO-$d_6$): δ=6.7 (s, 2H), 7.3-7.6 (m, 4H), 7.8 (s, 1H) ppm.

EXAMPLE 13A

5-Amino-1-(2-chlorophenyl)-1H-pyrazole-4-carbonitrile

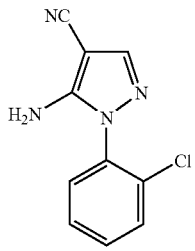

In analogy to the preparation of Example 10A, 4.64 g (78% of theory) of the desired product are obtained starting from 5.0 g (27.1 mmol) of 2-chlorophenylhydrazine hydrochloride, 3.31 g (27.1 mmol) of ethoxymethylenemalononitrile and 11.3 ml (81.3 mmol) of triethylamine.

m.p.: 135° C. MS (ESI pos): m/z=219 (M+H)$^{+1}$H-NMR (300 MHz, DMSO-d$_6$): δ=6.6 (s, 2H), 7.45-7.75 (m, 4H), 7.8 (s, 1H) ppm.

EXAMPLE 14A

5-Amino-1-(2-pyridinyl)-1H-pyrazole-4-carbonitrile

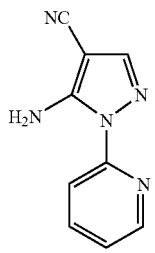

In analogy to the preparation of Example 10A, 2.3 g (46.6% of theory) of the desired product are obtained starting from 3.0 g (26.7 mmol, 97% purity) of 2-hydrazinopyridine, 3.26 g (26.7 mmol) of ethoxymethylenemalononitrile and 7.4 ml (53.3 mmol) of triethylamine.

m.p.: 193° C. MS (ESI pos): m/z=186 (M+H)$^{+1}$H-NMR (300 MHz, DMSO-d$_6$): δ=7.35 (m, 1H), 7.8-8.12 (m, 3H), 8.15 (s, 2H), 8.5 (m, 1H) ppm.

EXAMPLE 15A

5-Amino-1-(2-methoxyphenyl)-1H-pyrazole-4-carbonitrile

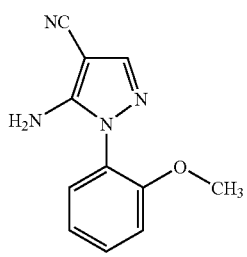

In analogy to the preparation of Example 10A, 3.5 g (88% of theory) of the desired product are obtained starting from 4.1 g (18 mmol) of 2-methoxyphenylhydrazine hydrochloride, 2.19 g (18 mmol) of ethoxymethylenemalononitrile and 10 ml (71.9 mmol) of triethylamine.

m.p.: 129° C. MS (ESI pos): m/z=215 (M+H)$^{+1}$H-NMR (300 MHz, DMSO-d$_6$): δ=3.8 (s, 3H), 6.3 (s, 2H), 7.05 (t, 1H), 7.2 (d, 1H), 7.5 (t, 1H), 7.7 (s, 1H) ppm.

EXAMPLE 16A

5-Amino-1-(2,6-dimethylphenyl)-1H-pyrazole-4-carboxamide

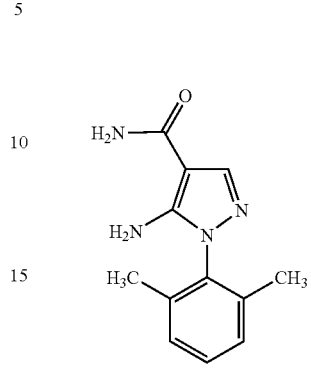

2 g (9.4 mmol) of 5-amino-1-(2,6-dimethylphenyl)-1H-pyrazole-4-carbonitrile (Example 1A) are dissolved in 25 ml of ethanol, and a mixture of 20 ml of 30% strength hydrogen peroxide and 40 ml of 25% strength ammonia is added. The solution is stirred at room temperature overnight and then concentrated to about 15 ml in a rotary evaporator. The oily emulsion resulting thereby is taken up in dichloromethane. It is washed several times with water and saturated sodium thiosulphate solution. Drying over magnesium sulphate is followed by removal of the solvent in vacuo. The residue is purified by preparative HPLC (YMC Gel ODS-AQ S 5/15 μm; eluent A: water, eluent B: acetonitrile; gradient: 0 min 30% B, 5 min 30% B, 50 min 95% B). 0.88 g (40% of theory) of the product is obtained as colourless solid.

LC-MS (Method 1): R$_t$=2.6 min. MS (ESI pos): m/z=231 (M+H)$^+$.

EXAMPLE 17A

5-Amino-1-(2,3-dimethylphenyl)-1H-pyrazole-4-carboxamide

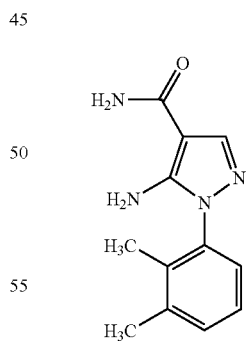

In analogy to the preparation of Example 16A, 1.29 g (70% of theory) of the desired product are obtained from 1.5 g (7.1 mmol) of 5-amino-1-(2,3-dimethylphenyl)-1H-pyrazole-4-carbonitrile (Example 2A) in a mixture of 25 ml of ethanol, 10 ml of 30% strength hydrogen peroxide and 40 ml of 25% strength ammonia.

LC-MS (Method 1): R$_t$=2.7 min. MS (ESI pos): m/z=231 (M+H)$^+$.

EXAMPLE 18A

5-Amino-1-(4-methylphenyl)-1H-pyrazole-4-carboxamide

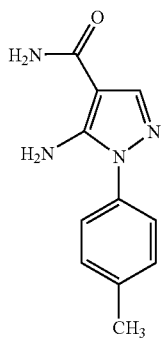

In analogy to the preparation of Example 16A, 1.02 g (47% of theory) of the desired product are obtained from 2 g (10.1 mmol) of 5-amino-1-(4-methylphenyl)-1H-pyrazole-4-carbonitrile (Example 3A) in a mixture of 25 ml of ethanol, 20 ml of 30% strength hydrogen peroxide and 40 ml of 25% strength ammonia.

LC-MS (Method 1): $R_t$=2.7 min. MS (ESI pos): m/z=217 (M+H)$^+$.

EXAMPLE 19A

5-Amino-1-(2,6-dichlorophenyl)-1H-pyrazole-4-carboxamide

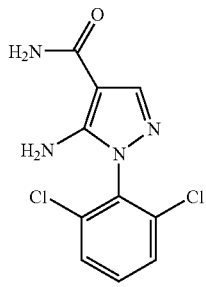

In analogy to the preparation of Example 16A, 1.6 g (74% of theory) of the desired product are obtained from 2 g (7.9 mmol) of 5-amino-1-(2,6-dichlorophenyl)-1H-pyrazole-4-carbonitrile (Example 4A) in a mixture of 25 ml of ethanol, 10 ml of 30% strength hydrogen peroxide and 40 ml of 25% strength ammonia by crystallization from the reaction solution.

LC-MS (Method 1): $R_t$=2.5 min. MS (ESI pos): m/z=271 (M+H)$^+$.

EXAMPLE 20A

5-Amino-1-(2,5-dichlorophenyl)-1H-pyrazole-4-carboxamide

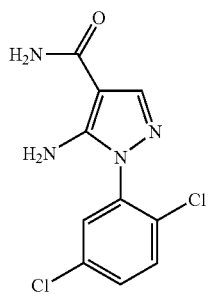

In analogy to the preparation of Example 16A, 2.02 g (94% of theory) of the desired product are obtained from 2 g (7.9 mmol) of 5-amino-1-(2,5-dichlorophenyl)-1H-pyrazole-4-carbonitrile (Example 5A) in a mixture of 25 ml of ethanol, 18 ml of 30% strength hydrogen peroxide and 40 ml of 25% strength ammonia by crystallization from the reaction solution.

LC-MS (Method 1): $R_t$=2.80 min. MS (ESI pos): m/z=271 (M+H)$^+$.

EXAMPLE 21A

5-Amino-1-(2-nitrophenyl)-1H-pyrazole-4-carboxamide

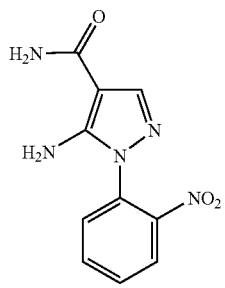

In analogy to the preparation of Example 16A, 1.4 g (86% of theory) of the desired product are obtained from 1.5 g (6.5 mmol) of 5-amino-1-(2-nitrophenyl)-1H-pyrazole-4-carbonitrile (Example 6A) in a mixture of 25 ml of ethanol, 16 ml of 30% strength hydrogen peroxide and 40 ml of 25% strength ammonia by crystallization from the reaction solution.

LC-MS (Method 1): $R_t$=2.3 min. MS (ESI pos): m/z=248 (M+H)$^+$.

EXAMPLE 22A

5-Amino-1-(2-aminophenyl)-1H-pyrazole-4-carboxamide

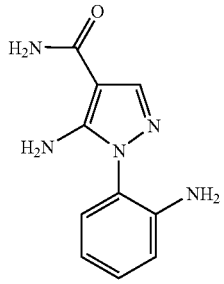

1.28 g (5.27 mmol) of 5-amino-1-(2-nitrophenyl)-1H-pyrazole-4-carboxamide (Example 21A) are introduced into 30 ml of ethyl acetate and stirred with 5.8 g (25.8 mmol) of tin(II) chloride dihydrate at 70° C. for 16 hours. After cooling to room temperature, the solution is adjusted to pH 9-10 with saturated sodium bicarbonate solution. The tin salts precipitated thereby are filtered off through kieselguhr. The filtrate is extracted with ethyl acetate. The combined organic phases are washed with saturated sodium chloride solution. After drying over sodium sulphate, the solvent is removed in vacuo. 0.82 g (72% of theory) of the desired product is obtained.

LC-MS (Method 2): $R_t$=3.0 min. MS (ESI pos): m/z=218 $(M+H)^+$ $^1$H-NMR (300 MHz, DMSO-$d_6$): δ=5.04 (s, 2H), 6.00 (s, 2H), 6.66 (m, 1H), 6.89 (m, 1H), 7.03 (m, 2H), 7.92 (s, 1H) ppm.

EXAMPLE 23A

5-Amino-1-(3-fluorophenyl)-1H-pyrazole-4-carboxamide

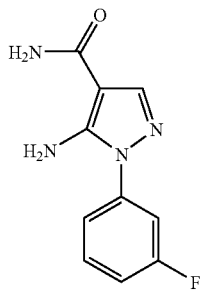

In analogy to the preparation of Example 16A, 1.1 g (75% of theory) of the desired product are obtained from 1.3 g (6.4 mmol) of 5-amino-1-(3-fluorophenyl)-1H-pyrazole-4-carbonitrile (Example 7A) in a mixture of 25 ml of ethanol, 10 ml of 30% strength hydrogen peroxide and 40 ml of 25% strength ammonia by crystallization from the reaction solution.

LC-MS (Method 1): $R_t$=2.60 min. MS (ESI pos): m/z=221 $(M+H)^+$.

EXAMPLE 24A

5-Amino-1-(3-chloropyridin-2-yl)-1H-pyrazole-4-carboxamide

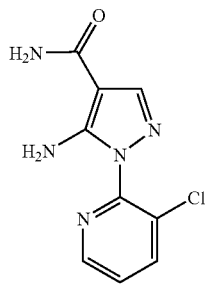

In analogy to the preparation of Example 16A, 0.29 g (66% of theory) of the desired product are obtained from 0.4 g (1.8 mmol) of 5-amino-1-(3-chloropyridin-2-yl)-1H-pyrazole-4-carbonitrile (Example 8A) in a mixture of 7 ml of ethanol, 5 ml of 30% strength hydrogen peroxide and 7 ml of 25% strength ammonia.

LC-MS (Method 2): $R_t$=3.00 min. MS (ESI pos): m/z=238 $(M+H)^+$. $^1$H-NMR (300 MHz, DMSO-$d_6$): δ=6.42 (s, 2H), 7.58 (dd, 1H), 7.88 (s, 1H), 8.20 (dd, 1H), 8.53 (dd, 1H) ppm.

EXAMPLE 25A

5-Amino-1-(2-methylphenyl)-1H-pyrazole-4-carboxamide

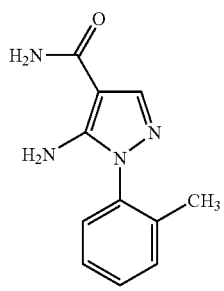

300 ml of 96% strength sulphuric acid are cautiously added to 40.0 g (201.8 mmol) of 5-amino-1-(2-methylphenyl)-1H-pyrazole-4-carbonitrile (Example 9A) while cooling in ice. The mixture is then heated to 40° C. and stirred for 2 hours at this temperature. After cooling, it is poured into 2 l of ice-water and cautiously neutralized with 50% strength sodium hydroxide solution. After extraction with ethyl acetate three times (2 l each time) the combined organic phases are washed with saturated sodium chloride solution and dried over sodium sulphate, and the solvent is distilled off under reduced pressure. 36.0 g (82% of theory) of product (purity >90%) are obtained and are employed without further purification in subsequent reactions.

LC-MS (Method 6): $R_t$=2.14 min. MS (ESI pos): m/z=217 $(M+H)^+$.

EXAMPLE 26A

5-Amino-1-(2-ethylphenyl)-1H-pyrazole-4-carboxamide

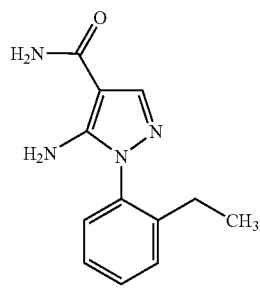

In analogy to the preparation of Example 16A, 2.58 g (87% of theory) of the desired product are obtained from 2.75 g (12.8 mmol) of 5-amino-1-(2-ethylphenyl)-1H-pyrazole-4-carbonitrile (Example 10A) in a mixture of 106 ml of ethanol, 27 ml of 30% strength hydrogen peroxide and 133 ml of 25% strength ammonia after chromatography on silica gel (mobile phase dichloromethane with 0-10% methanol).

m.p.: 147° C. MS (ESI pos): m/z=231 (M+H)$^{+1}$H-NMR (300 MHz, DMSO-d$_6$): δ=1.0 (t, 3H), 2.4 (q, 2H), 5.95 (s, 2H), 6.3 (broad d, 2H), 7.2-7.5 (m, 4H), 7.8 (s, 1H) ppm.

EXAMPLE 27A

5-Amino-1-(2-trifluoromethylphenyl)-1H-pyrazole-4-carboxamide

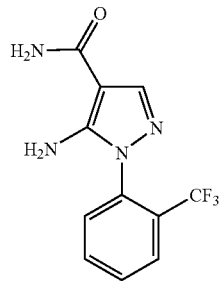

In analogy to the preparation of Example 16A, 4.01 g (87% of theory) of the desired product are obtained from 5.0 g (19.8 mmol) of 5-amino-1-(2-trifluoromethylphenyl)-1H-pyrazole-4-carbonitrile (Example 11A) in a mixture of 195 ml of ethanol, 49 ml of 30% strength hydrogen peroxide and 244 ml of 25% strength ammonia after chromatography on silica gel (mobile phase dichloromethane with 0-10% methanol).

m.p.: 186° C. MS (ESI pos): m/z=271 (M+H)$^{+1}$H-NMR (300 MHz, DMSO-d$_6$): δ=6.1 (s, 2H), 7.0 (broad d, 2H), 7.45-8.0 (m, 5H) ppm.

EXAMPLE 28A

5-Amino-1-(2-fluorophenyl)-1H-pyrazole-4-carboxamide

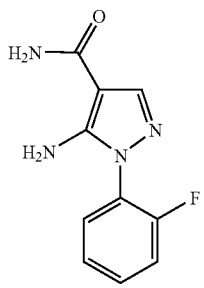

In analogy to the preparation of Example 16A, 3.89 g (81% of theory) of the desired product are obtained from 5.0 g (21.9 mmol, 89% purity) of 5-amino-1-(2-fluorophenyl)-1H-pyrazole-4-carbonitrile (Example 12A) in a mixture of 173 ml of ethanol, 43 ml of 30% strength hydrogen peroxide and 216 ml of 25% strength ammonia after chromatography on silica gel (mobile phase dichloromethane with 0-10% methanol).

m.p.: 181° C. MS (ESI pos): m/z=221 (M+H)$^{+1}$H-NMR (300 MHz, DMSO-d$_6$): δ=6.2 (s, 2H), 7.0 (broad d, 2H), 7.3-7.6 (m, 4H), 7.9 (s, 1H) ppm.

EXAMPLE 29A

5-Amino-1-(2-chlorophenyl)-1H-pyrazole-4-carboxamide

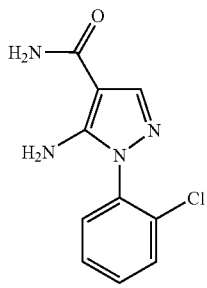

In analogy to the preparation of Example 16A, 3.93 g (79% of theory) of the desired product are obtained from 4.6 g (21.0 mmol) of 5-amino-1-(2-chlorophenyl)-1H-pyrazole-4-carbonitrile (Example 13A) in a mixture of 159 ml of ethanol, 39 ml of 30% strength hydrogen peroxide and 198 ml of 25% strength ammonia after chromatography on silica gel (mobile phase dichloromethane with 0-10% methanol).

m.p.: 166° C. MS (ESI pos): m/z=237 (M+H)+ 1H-NMR (300 MHz, DMSO-d6): δ=6.1 (s, 2H), 7.0 (broad d, 2H), 7.4-7.7 (m, 4H), 7.85 (s, 1H) ppm.

EXAMPLE 30A

5-Amino-1-(2-pyridinyl)-1H-pyrazole-4-carboxamide

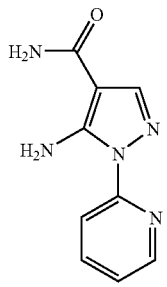

In analogy to the preparation of Example 16A, 2.28 g (90% of theory) of the desired product are obtained from 2.3 g (12.4 mmol) of 5-amino-1-(2-pyridinyl)-1H-pyrazole-4-carbonitrile (Example 14A) in a mixture of 90 ml of ethanol, 23 ml of 30% strength hydrogen peroxide and 113 ml of 25% strength ammonia after chromatography on silica gel (mobile phase dichloromethane with 0-10% methanol).

m.p.: 218° C. MS (DCI): m/z=204 (M+H)+ 1H-NMR (300 MHz, DMSO-d6): δ=7.1 (broad d, 2H), 7.3 (dd, 1H), 7.5 (s, 2H), 7.85 (d, 1H), 7.95 (s, 1H), 8.0 (dd, 1H), 8.45 (d, 1H) ppm.

EXAMPLE 31A

5-Amino-1-(2-methoxyphenyl)-1H-pyrazole-4-carboxamide

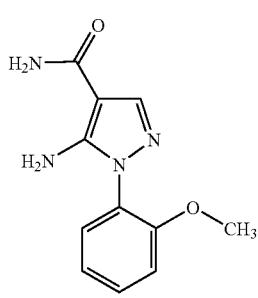

In analogy to the preparation of Example 16A, 2.61 g (70% of theory) of the desired product are obtained from 3.5 g (16.0 mmol, 98% purity) of 5-amino-1-(2-methoxyphenyl)-1H-pyrazole4-carbonitrile (Example 15A) in a mixture of 172 ml of ethanol, 34 ml of 30% strength hydrogen peroxide and 137 ml of 25% strength ammonia after chromatography on silica gel (mobile phase dichloromethane with 0-10% methanol).

m.p.: 191° C. MS (ESI pos): m/z=233 (M+H)+ 1H-NMR (300 MHz, DMSO-d6): δ=3.8 (s, 3H), 5.9 (s, 2H), 7.0 (broad s, 2H), 7.05-7.55 (m, 4H), 7.8 (s, 1H) ppm.

Exemplary Embodiments

EXAMPLE 1

6-(3-Chlorobenzyl)-1-(2,6-dimethylphenyl)-1,5-dihydropyrazolo[3,4-d]pyrimidin-4-one

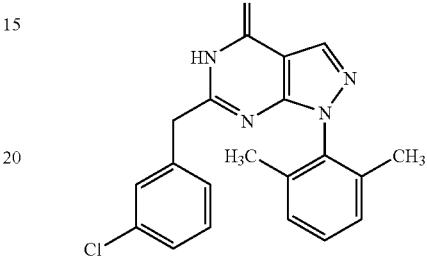

0.1 g (0.43 mmol) of 5-amino-1-(2,6-dimethylphenyl)-1H-pyrazole-4-carboxamide (Example 16A) is dissolved under argon in 6 ml of absolute ethanol and 0.24 g (1.3 mmol) of methyl 3-chlorophenylacetate and 0.17 g (4.34 mmol) of 60% sodium hydride (suspension in mineral oil) are added. The reaction mixture is heated to reflux overnight. Cooling to room temperature is followed by acidification with concentrated hydrochloric acid. The sodium chloride precipitated thereby is filtered off. The filtrate is concentrated in vacuo, and the remaining residue is purified by preparative HPLC (YMC Gel ODS-AQ S 5/15 μm; eluent A: water, eluent B: acetonitrile; gradient: 0 min 30% B, 5 min 30% B, 50 min 95% B). 59 mg (37% of theory) of the product are obtained as a colourless solid.

LC-MS (Method 2): $R_t$=4.20 min. MS (ESI pos): m/z=365 (M+H)+ 1H-NMR (300 MHz, DMSO-d6): δ=1.87 (s, 6H), 3.92 (s, 2H), 7.29 (m, 7H), 8.28 (s, 1H), 12.43 (s, 1H) ppm.

EXAMPLE 2

6-(3-Chlorobenzyl)-1-(2,3-dimethylphenyl)-1,5-dihydropyrazolo[3,4-d]pyrimidin-4-one

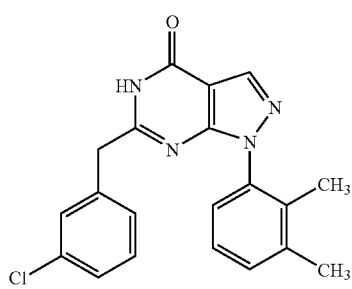

0.1 g (0.43 mmol) of 5-amino-1-(2,3-dimethylphenyl)-1H-pyrazole-4-carboxamide (Example 17A) is dissolved under argon in 6 ml of absolute ethanol and 0.24 g (1.3 mmol) of methyl 3-chlorophenylacetate and 0.17 g (4.34 mmol) of 60% sodium hydride (suspension in mineral oil) are added. The reaction mixture is heated to reflux overnight. Cooling to room temperature is followed by acidification with concentrated hydrochloric acid. The mixture of sodium chloride and the product precipitated thereby is filtered off and washed several times with water and diethyl ether. Drying under high vacuum results in 97 mg (61% of theory) of the product as colourless solid.

LC-MS (Method 3): $R_t$=3.85 min. MS (ESI pos): m/z=365 $(M+H)^+$ $^1$H-NMR (300 MHz, DMSO-$d_6$): δ=1.82 (s, 3H), 2.32 (s, 3H), 3.92 (s, 2H), 7.31 (m, 7H), 8.23 (s, 1H), 12.40 (s, 1H) ppm.

EXAMPLE 3

6-(3-Chlorobenzyl)-1-(4-methylphenyl)-1,5-dihydropyrazolo[3,4-d]pyrimidin-4-one

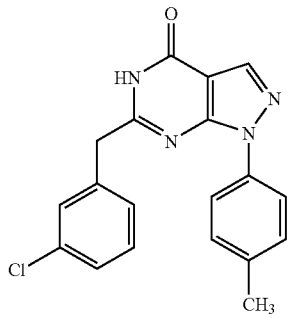

In analogy to the preparation of Example 2, 99 mg (69% of theory) of the desired product are obtained as a colourless solid starting from 0.88 g (0.41 mmol) of 5-amino-1-(4-methylphenyl)-1H-pyrazole-4-carboxamide (Example 18A), 0.22 g (1.2 mmol) of methyl 3-chlorophenylacetate and 0.16 g (4.09 mmol) of 60% sodium hydride.

LC-MS (Method 3): $R_t$=4.03 min. MS (ESI pos): m/z=351 $(M+H)^+$ $^1$H-NMR (300 MHz, DMSO-$d_6$): δ=2.35 (s, 3H), 4.04 (s, 2H), 7.35 (m, 5H), 7.50 (s, 1H), 7.89 (d, 2H), 8.23 (s, 1H), 12.49 (s, 1H) ppm.

EXAMPLE 4

6-(3-Chlorobenzyl)-1-(2,6-dichlorophenyl)-1,5-dihydropyrazolo[3,4-d]pyrimidin-4-one

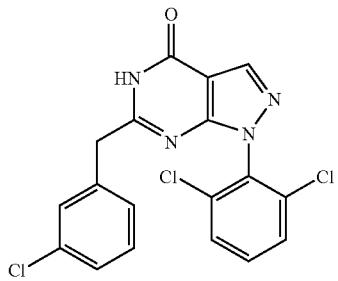

In analogy to the preparation of Example 1, 104 mg (69% of theory) of the desired product are obtained as a colourless solid starting from 0.1 g (0.37 mmol) of 5-amino-1-(2,6-dichlorophenyl)-1H-pyrazole-4-carboxamide (Example 19A), 0.2 g (1.1 mmol) of methyl 3-chlorophenylacetate and 0.14 g (3.6 mmol) of 60% sodium hydride.

LC-MS (Method 3): $R_t$=3.77 min. MS (ESI pos): m/z=405 $(M+H)^+$ $^1$H-NMR (300 MHz, DMSO-$d_6$): δ=3.94 (s, 2H), 7.30 (m, 4H), 7.69 (m, 2H), 7.70 (s, 1H), 8.39 (s, 1H), 12.57 (s, 1H) ppm.

EXAMPLE 5

6-(3-Chlorobenzyl)-1-(2,5-dichlorophenyl)-1,5-dihydropyrazolo[3,4-d]pyrimidin-4-one

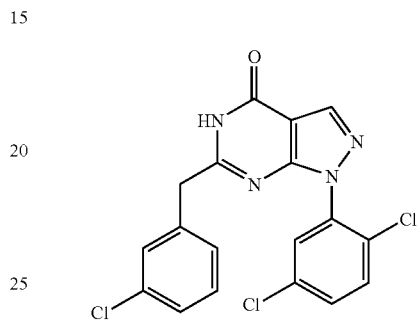

In analogy to the preparation of Example 1, 35 mg (23% of theory) of the desired product are obtained as a colourless solid starting from 0.1 g (0.37 mmol) of 5-amino-1-(2,5-dichlorophenyl)-1H-pyrazole-4-carboxamide (Example 20A), 0.2 g (1.1 mmol) of methyl 3-chlorophenylacetate and 0.14 g (3.6 mmol) of 60% sodium hydride.

LC-MS (Method 2): $R_t$=4.20 min. MS (ESI pos): m/z=405 $(M+H)^+$

EXAMPLE 6

1-(2-Aminophenyl)-6-(3-chlorobenzyl)-1,5-dihydropyrazolo[3,4-d]pyrimidin-4-one

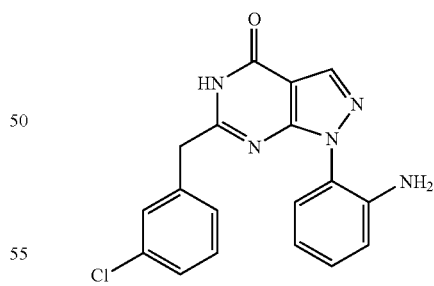

In analogy to the preparation of Example 1, 103 mg (63% of theory) of the desired product are obtained as a colourless solid starting from 0.1 g (0.46 mmol) of 5-amino-1-(2-aminophenyl)-1H-pyrazole-4-carboxamide (Example 22A), 0.25 g (1.4 mmol) of methyl 3-chlorophenylacetate and 0.18 g (4.6 mmol) of 60% sodium hydride.

LC-MS (Method 6): $R_t$=3.32 min. MS (ESI pos): m/z=352 $(M+H)^+$ $^1$H-NMR (300 MHz, DMSO-$d_6$): δ=3.96 (s, 2H), 4.46 (s, 2H), 6.81 (t, 1H), 7.03 (d, 1H), 7.31 (m, 5H), 7.44 (s, 1H), 8.28 (s, 1H), 12.47 (s, 1H) ppm.

EXAMPLE 7

6-(3-Chlorobenzyl)-1-(3-fluorophenyl)-1,5-dihydro-pyrazolo[3,4-d]pyrimidin-4-one

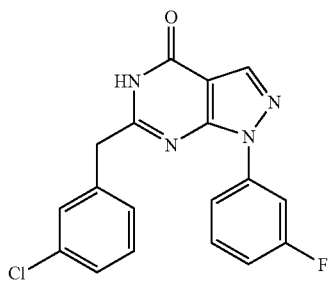

In analogy to the preparation of Example 2, 125 mg (77% of theory) of the desired product are obtained as a colourless solid starting from 0.1 g (0.45 mmol) of 5-amino-1-(3-fluorophenyl)-1H-pyrazole-4-carboxamide (Example 23A), 0.25 g (1.36 mmol) of methyl 3-chlorophenylacetate and 0.18 g (4.5 mmol) of 60% sodium hydride.

LC-MS (Method 3): $R_t$=3.98 min. MS (ESI pos): m/z=355 (M+H)$^{+1}$H-NMR (300 MHz, DMSO-d$_6$): δ=4.08 (s, 2H), 7.19 (m, 1H), 7.36 (m, 3H), 7.55 (m, 2H), 7.93 (m, 2H), 8.3 (s, 1H), 12.61 (s, 1H) ppm.

EXAMPLE 8

6-(3-Chlorobenzyl)-1-(3-chloropyridin-2-yl)-1,5-dihydropyrazolo[3,4-d]pyrimidin-4-one

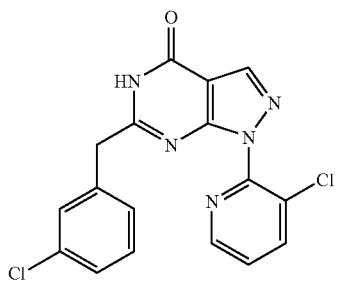

In analogy to the preparation of Example 2, 85 mg (54% of theory) of the desired product are obtained as a colourless solid starting from 0.1 g (0.42 mmol) of 5-amino-1-(3-chloropyridin-2-yl)-1H-pyrazole-4-carboxamide (Example 24A), 0.23 g (1.26 mmol) of methyl 3-chlorophenylacetate and 0.17 g (4.2 mmol) of 60% sodium hydride.

LC-MS (Method 3): $R_t$=3.10 min. MS (ESI pos): m/z=372 (M+H)$^{+1}$H-NMR (300 MHz, DMSO-d$_6$): δ=4.01 (s, 2H), 7.34 (m, 4H), 7.49 (s, 1H), 7.69 (d, 1H), 7.91 (t, 1H), 8.27 (s, 1H), 12.57 (s, 1H) ppm.

EXAMPLE 9

6-(2-Bromobenzyl)-1-(2-methylphenyl)-1,5-dihydro-pyrazolo[3,4-d]pyrimidin-4-one

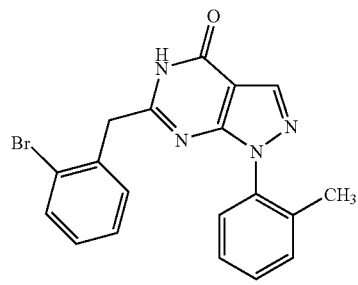

2.0 g (9.25 mmol) of 5-amino-1-(2-methylphenyl)-1H-pyrazole-4-carboxamide (Example 25A) and 9.5 g (41.62 mmol) of methyl (2-bromophenyl)acetate are dissolved in 30 ml of absolute ethanol under argon, and 3.15 g (46.6 mmol) of sodium ethoxide are added. The reaction mixture is heated to a reflux overnight. Cooling to room temperature is followed by hydrolysis with 50 ml of water and subsequent extraction with ethyl acetate (2×50 ml). The combined organic phases are dried over sodium sulphate, and the solvent is distilled off under reduced pressure. The crude product is then purified by column chromatography (silica gel; mobile phase cyclohexane/ethyl acetate, gradient 10:1→1:1). 3.01 g (82% of theory) of the product are obtained.

LC-MS (Method 5): $R_t$=3.27 min. MS (ESI pos): m/z=395 (M+H)$^{+1}$H-NMR (300 MHz, DMSO-d$_6$): δ=1.96 (s, 3H), 4.09 (s, 2H), 7.14-7.40 (7H), 7.59 (dd, 1H), 8.26 (s, 1H), 12.55 (s, 1H) ppm.

EXAMPLE 10

6-(3-Bromobenzyl)-1-(2-methylphenyl)-1,5-dihydro-pyrazolo[3,4-d]pyrimidin-4-one

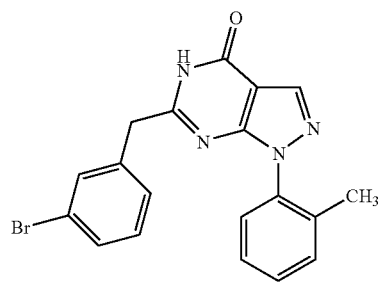

813 mg (3.78 mmol) of 5-amino-1-(2-methylphenyl)-1H-pyrazole-4-carboxamide (Example 25A) and 3.90 g (17.03 mmol) of methyl (3-bromophenyl)acetate are dissolved in 15 ml of absolute ethanol under argon, and 1.29 g (18.9 mmol) of sodium ethoxide are added. The reaction mixture is heated to a reflux overnight. Cooling to room temperature is followed by hydrolysis with 25 ml of water and subsequent extraction with ethyl acetate (2×25 ml). The combined organic phases are dried over sodium sulphate, and the solvent is distilled off under reduced pressure. The crude product is then purified by column chromatography (silica gel; mobile phase cyclohexane/ethyl acetate, gradient 10:1→1:1). 1.33 g (89% of theory) of the product are obtained.

LC-MS (Method 5): $R_t$=3.34 min. MS (ESI pos): m/z=395 (M+H)$^+$ $^1$H-NMR (300 MHz, DMSO-d$_6$): δ=2.03 (s, 3H), 3.92 (s, 2H), 7.24-7.51 (7H), 7.56 (m, 1H), 8.22 (s, 1H), 12.45 (s, 1H) ppm.

Exemplary embodiments 11-15 listed in Table 1 below are prepared in analogy to the method of Example 10 starting from 100 mg (0.46 mmol) of 5-amino-1-(2-methylphenyl)-1H-pyrazole-4-carboxamide (Example 25A) with 157 mg (2.31 mmol) of sodium ethoxide and with 2.08 mmol of the ester specified in the table. The crude product is purified in each case via preparative HPLC.

TABLE 1

| Ex. No. | Structure | Precursors | Yield [%] | $R_t$ [min] (method) | MS: m/z [M + H]$^+$ |
|---|---|---|---|---|---|
| 11 | 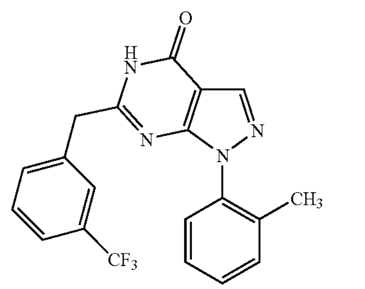 | Example 25A, Methyl (3-trifluoromethylphenyl)acetate | 60.1 | 2.04 (4) | 385 |
| 12 | 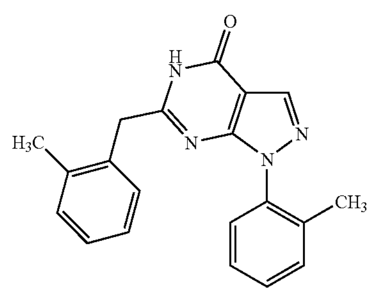 | Example 25A, Methyl (2-methylphenyl)acetate | 43.9 | 2.00 (4) | 331 |
| 13 | 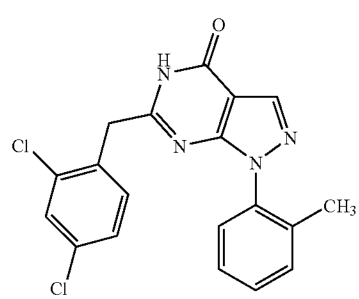 | Example 25A, Methyl (2,4-dichlorophenyl)acetate | 39.2 | 2.15 (4) | 386 |
| 14 | 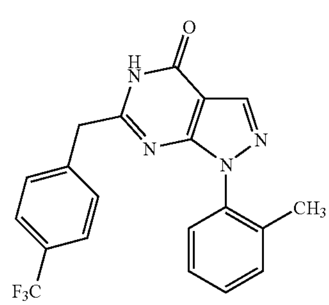 | Example 25A, Methyl (4-trifluoromethylphenyl)acetate | 12.0 | 2.05 (4) | 385 |

TABLE 1-continued

| Ex. No. | Structure | Precursors | Yield [%] | $R_t$ [min] (method) | MS: m/z $[M + H]^+$ |
|---|---|---|---|---|---|
| 15 | 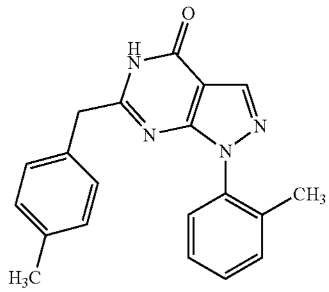 | Example 25A, Methyl (4-methylphenyl)-acetate | 34.8 | 1.98 (4) | 331 |

EXAMPLE 16

6-(3-Chlorobenzyl)-1-(2-methylphenyl)-1,5-dihydro-4H-pyrazolo[3,4-d]pyrimidin-4-one

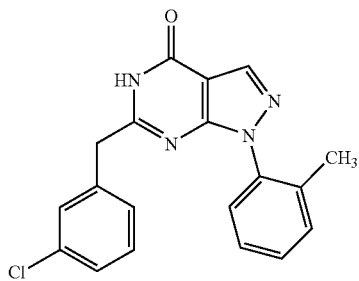

In analogy to the preparation of Example 9, 146 mg (60% of theory) of the desired product are obtained as a colourless solid starting from 0.15 g (0.69 mmol) of 5-amino-1-(2-methylphenyl)-1H-pyrazole-4-carboxamide (Example 25A), 0.482 g (2.43 mmol) of ethyl (3-chlorophenyl)acetate and 0.139 g (3.47 mmol) of 60% sodium hydride.

m.p.: 215° C. MS (ESI pos): m/z=351 (M+H)$^{+1}$H-NMR (300 MHz, DMSO-d$_6$): δ=2.05 (s, 3H), 3.9 (s, 2H), 7.2-7.5 (m, 8H), 8.25 (s, 1H), 12.5 (s, 1H) ppm.

EXAMPLE 17

1-(2-Methylphenyl)-6-(2-pyridinylmethyl)-1,5-dihydro-4H-pyrazolo[3,4-d]pyrimidin-4-one

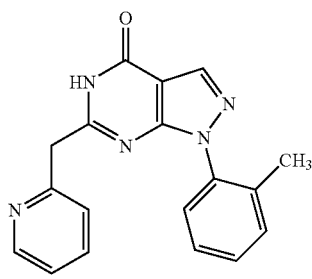

In analogy to the preparation of Example 9, 71 mg (40% of theory) of the desired product are obtained as a colourless solid starting from 0.12 g (0.55 mmol) of 5-amino-1-(2-methylphenyl)-1H-pyrazole-4-carboxamide (Example 25A), 0.252 g (1.66 mmol) of ethyl (2-pyridinyl)acetate and 0.111 g (2.77 mmol) of 60% sodium hydride.

m.p.: 162° C. MS (ESI pos): m/z=318 (M+H)$^{+1}$H-NMR (300 MHz, DMSO-d$_6$): δ=2.0 (s, 3H), 4.2 (s, 2H), 7.2-7.5 (m, 6H), 7.8 (t, 1H), 8.25 (s, 1H), 8.5 (d, 1H), 12.4 (s, 1H) ppm.

EXAMPLE 18

6-(3-Chlorobenzyl)-1-(2-ethylphenyl)-1,5-dihydro-4H-pyrazolo[3,4-d]pyrimidin-4-one

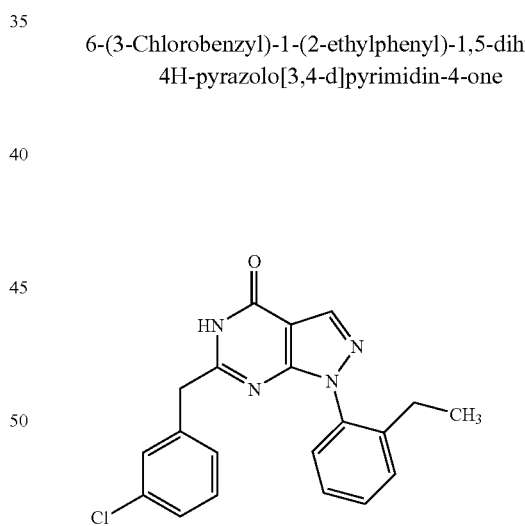

In analogy to the preparation of Example 9, 65 mg (27% of theory) of the desired product are obtained as a colourless solid starting from 0.15 g (0.65 mmol) of 5-amino-1-(2-ethylphenyl)-1H-pyrazole-4-carboxamide (Example 26A), 0.398 g (1.95 mmol) of ethyl (3-chlorophenyl)acetate and 0.130 g (3.26 mmol) of 60% sodium hydride.

m.p.: 208° C. MS (ESI pos): m/z=365 (M+H)$^{+1}$H-NMR (300 MHz, DMSO-d$_6$): δ=0.9 (t, 3H), 2.35 (q, 2H), 3.9 (s, 2H), 7.15-7.5 (m, 8H), 8.25 (s, 1H), 12.45 (s, 1H) ppm.

EXAMPLE 19

6-(3-Chlorobenzyl)-1-(2-trifluoromethylphenyl)-1,5-dihydro-4H-pyrazolo[3,4-d]pyrimidin-4-one

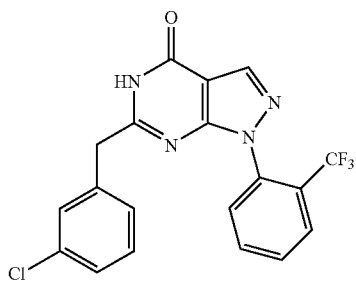

In analogy to the preparation of Example 9, 157 mg (70% of theory) of the desired product are obtained as a colourless solid starting from 0.15 g (0.56 mmol) of 5-amino-1-(2-trifluoromethylphenyl)-1H-pyrazole-4-carboxamide (Example 27A), 0.339 g (1.67 mmol) of ethyl (3-chlorophenyl)acetate and 0.111 g (2.78 mmol) of 60% sodium hydride.

m.p.: 152° C. MS (ESI pos): m/z=405 (M+H)$^{+1}$H-NMR (300 MHz, DMSO-d$_6$): δ=3.9 (s, 2H), 7.15-7.5 (m, 4H), 7.6-8.05 (m, 4H), 8.3 (s, 1H), 12.5 (s, 1H) ppm.

EXAMPLE 20

6-(3-Chlorobenzyl)-1-(2-fluorophenyl)-1,5-dihydro-4H-pyrazolo[3,4-d]pyrimidin-4-one

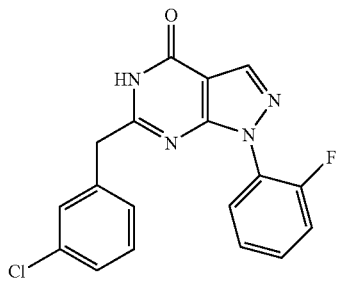

In analogy to the preparation of Example 9, 171 mg (73% of theory) of the desired product are obtained as a colourless solid starting from 0.15 g (0.66 mmol) of 5-amino-1-(2-fluorophenyl)-1H-pyrazole-4-carboxamide (Example 28A), 0.405 g (98% purity, 1.99 mmol) of ethyl (3-chlorophenyl) acetate and 0.132 g (3.32 mmol) of 60% sodium hydride.

m.p.: 197° C. MS (ESI pos): m/z=355 (M+H)$^{+1}$H-NMR (300 MHz, DMSO-d$_6$):δ=3.95 (s, 2H), 7.2-7.7 (m, 8H), 8.3 (s, 1H), 12.5 (s, 1H) ppm.

EXAMPLE 21

6-(3-Chlorobenzyl)-1-(2-chlorophenyl)-1,5-dihydro-4H-pyrazolo[3,4-d]pyrimidin-4-one

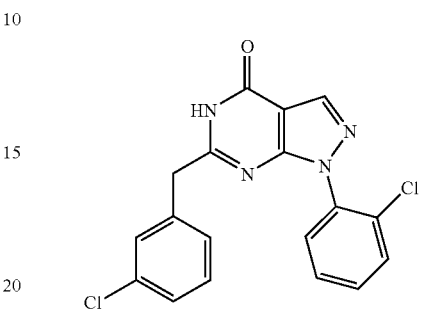

In analogy to the preparation of Example 9, 160 mg (70% of theory) of the desired product are obtained as a colourless solid starting from 0.15 g (0.63 mmol) of 5-amino-1-(2-chlorophenyl)-1H-pyrazole-4-carboxamide (Example 29A), 0.387 g (98% purity, 1.90 mmol) of ethyl (3-chlorophenyl) acetate and 0.127 g (3.17 mmol) of 60% sodium hydride.

m.p.: 188° C. MS (ESI pos): m/z=372 (M+H)$^{+1}$H-NMR (300 MHz, DMSO-d$_6$): δ=3.9 (s, 2H), 7.2-7.75 (m, 8H), 8.3 (s, 1H), 12.5 (s, 1H) ppm.

EXAMPLE 22

6-(3-Chlorobenzyl)-1-(2-pyridinyl)-1,5-dihydro-4H-pyrazolo[3,4-d]pyrimidin-4-one

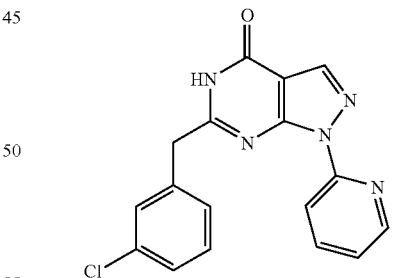

In analogy to the preparation of Example 9, 103 mg (41% of theory) of the desired product are obtained as a colourless solid starting from 0.15 g (0.74 mmol) of 5-amino-1-(2-pyridinyl)-1H-pyrazole-4-carboxamide (Example 30A), 0.451 g (98% purity, 2.21 mmol) of ethyl (3-chlorophenyl)acetate and 0.148 g (3.69 mmol) of 60% sodium hydride.

m.p.: 230° C. MS (ESI pos): m/z=338 (M+H)$^{+1}$H-NMR (300 MHz, DMSO-d$_6$): δ=4.0 (s, 2H), 7.2-7.75 (m, 5H), 7.9-8.05 (m, 2H), 8.3 (s, 1H), 8.6 (d, 1H), 12.5 (s, 1H) ppm.

EXAMPLE 23

6-(3-Chlorobenzyl)-1-(2-methoxyphenyl)-1,5-dihydro-4H-pyrazolo[3,4-d]pyrimidin-4-one

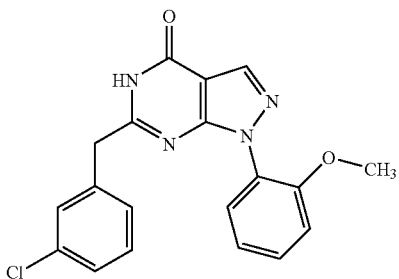

In analogy to the preparation of Example 9, 180 mg (76% of theory) of the desired product are obtained as a colourless solid starting from 0.15 g (0.65 mmol) of 5-amino-1-(2-methoxyphenyl)-1H-pyrazole-4-carboxamide (Example 31A), 0.394 g (98% purity, 1.94 mmol) of ethyl (3-chlorophenyl) acetate and 0.129 g (3.23 mmol) of 60% sodium hydride.

m.p.: 196° C. MS (ESI pos): m/z=367 (M+H)$^{+1}$H-NMR (300 MHz, DMSO-d$_6$): δ=3.7 (s, 3H), 3.9 (s, 2H), 7.0-7.6 (m, 8H), 8.2 (s, 1H), 12.4 (s, 1H) ppm.

The invention claimed is:
1. A compound of the formula (I):

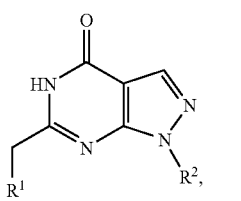

in which

R$^1$ is phenyl, pyridyl or thiophenyl which are optionally substituted by up to 3 substituents independently of one another selected from the group of C$_1$-C$_6$-alkyl, C$_1$-C$_6$-alkoxy, hydroxycarbonyl, cyano, trifluoromethyl, amino, nitro, hydroxy, C$_1$-C$_6$-alkylamino, halogen, C$_6$-C$_{10}$-arylcarbonylamino, C$_1$-C$_6$-alkylcarbonylamino, C$_1$-C$_6$-alkylaminocarbonyl, C$_1$-C$_6$-alkoxycarbonyl, C$_6$-C$_{10}$-arylaminocarbonyl, heteroarylaminocarbonyl, heteroarylcarbonylamino, C$_1$-C$_6$-alkylsulphonylamino, C$_1$-C$_6$-alkylsulphonyl, C$_1$-C$_6$-alkylthio, where C$_1$-C$_6$-alkyl, C$_1$-C$_6$-alkoxy, C$_1$-C$_6$-alkylamino, C$_6$-C$_{10}$-arylcarbonylamino, C$_1$-C$_6$-alkylcarbonylamino, C$_1$-C$_6$-alkylaminocarbonyl, C$_1$-C$_6$-alkoxycarbonyl, C$_6$-C$_{10}$-arylaminocarbonyl, heteroarylaminocarbonyl, heteroarylcarbonylamino, C$_1$-C$_6$-alkylsulphonylamino, C$_1$-C$_6$-alkyl-sulphonyl and C$_1$-C$_6$-alkylthio are optionally substituted by a radical selected from the group of hydroxy, cyano, halogen, hydroxycarbonyl and a group of the formula —NR$^3$R$^4$, where R$^3$ and R$^4$ are independently of one another hydrogen or C$_1$-C$_6$-alkyl, or R$^3$ and R$^4$ together with the nitrogen atom to which they are bonded are 5- to 8-membered heterocyclyl, R$^2$ is phenyl or heteroaryl, where phenyl is substituted by 1 to 3 radicals and heteroaryl is optionally substituted by 1 to 3 radicals in each case independently of one another selected from the group of C$_1$-C$_6$-alkyl, C$_1$-C$_6$-alkoxy, hydroxycarbonyl, cyano, trifluoromethyl, amino, nitro, hydroxy, C$_1$-C$_6$-alkylamino, halogen, C$_6$-C$_{10}$-arylcarbonylamino, C$_1$-C$_6$-alkylcarbonylamino, C$_1$-C$_6$-alkylaminocarbonyl, C$_1$-C$_6$-alkoxycarbonyl, C$_6$-C$_{10}$-arylaminocarbonyl, heteroarylaminocarbonyl, heteroarylcarbonylamino, C$_1$-C$_6$-alkylsulphonylamino, C$_1$-C$_6$-alkylsulphonyl and C$_1$-C$_6$-alkylthio, where C$_1$-C$_6$-alkyl, C$_1$-C$_6$-alkoxy, C$_1$-C$_6$-alkylamino, C$_6$-C$_{10}$-arylcarbonylamino, C$_1$-C$_6$-alkylcarbonylamino, C$_1$-C$_6$-alkylaminocarbonyl, C$_1$-C$_6$-alkoxycarbonyl, C$_6$-C$_{10}$-arylaminocarbonyl, heteroarylaminocarbonyl, hetero-arylcarbonylamino, C$_1$-C$_6$-alkylsulphonylamino, C$_1$-C$_6$-alkylsulphonyl and C$_1$-C$_6$-alkylthio are optionally substituted by a radical independently of one another selected from the group of hydroxy, cyano, halogen, hydroxy-carbonyl and a group of the formula —NR$^3$R$^4$, where R$^3$ and R$^4$ the meanings indicated above, or a salt thereof.

2. The compound of claim 1, where

R$^1$ is phenyl, pyridyl or thiophenyl, which are optionally substituted by up to 3 radicals independently of one another selected from the group of C$_1$-C$_4$-alkyl, C$_1$-C$_4$-alkoxy, hydroxycarbonyl, cyano, trifluoromethyl, amino, hydroxy, C$_1$-C$_4$- alkylamino, fluorine, chlorine, bromine, C$_6$-C$_{10}$-arylcarbonylamino, C$_1$-C$_4$-alkyl-carbonylamino, C$_1$-C$_4$-alkylaminocarbonyl, C$_1$-C$_4$-alkoxycarbonyl, C$_6$-C$_{10}$-aryl-aminocarbonyl, heteroarylaminocarbonyl, heteroarylcarbonylamino, C$_1$-C$_4$-alkyl-sulphonylamino, C$_1$-C$_4$-alkylsulphonyl, C$_1$-C$_4$-alkylthio, where C$_1$-C$_4$-alkyl and C$_1$-C$_4$-alkoxy are optionally substituted by a radical selected from the group of hydroxy, cyano, fluorine, chlorine, bromine, hydroxycarbonyl and a group of the formula —NR$^3$R$^4$, where R$^3$ and R$^4$ are independently hydrogen or C$_1$-C$_4$-alkyl, or R$^3$ and R$^4$ together with the nitrogen atom to which they are bonded are 5-to 6-membered heterocyclyl, R$^2$ is phenyl, pyrimidyl or pyridyl, where phenyl is substituted by 1 to 3 radicals and pyrimidyl and pyridyl are optionally substituted by 1 to 3 radicals in each case independently of one another selected from the group of C$_1$-C$_4$-alkyl, C$_1$-C$_4$-alkoxy, hydroxycarbonyl, cyano, trifluoromethyl, amino, hydroxy, C$_1$-C$_4$-alkyl-amino, fluorine, chlorine, bromine, C$_6$-C$_{10}$-arylcarbonylamino, C$_1$-C$_4$-alkyl-carbonylamino, C$_1$-C$_4$-alkylaminocarbonyl, C$_1$-C$_4$-alkoxycarbonyl, C$_6$-C$_{10}$-aryl-aminocarbonyl, heteroarylaminocarbonyl, heteroarylcarbonylamino, C$_1$-C$_4$-alkylsulphonylamino, C$_1$-C$_4$-alkylsulphonyl, C$_1$-C$_4$-alkylthio, where C$_1$-C$_4$-alkyl and C$_1$-C$_4$-alkoxy are optionally substituted by a radical selected from the group of hydroxy, cyano, fluorine, chlorine, bromine, hydroxycarbonyl and a group of the formula —NR$^3$R$^4$, where R$^3$ and R$^4$ the meanings indicated in claim 1, or a salt thereof.

3. The compound of claim 1, where
R$^1$ has the meanings indicated in claim 1, and
R$^2$ is phenyl or pyridyl, where phenyl is substituted by 1 to 2 radicals and pyridyl is optionally substituted by 1 to 2 radicals in each case independently of one another selected from the group of methyl, ethyl, 2-propyl, trifluoromethyl, methoxy, ethoxy, fluorine and chlorine,
or a salt thereof.

4. The compound of claim 1, where
R$^1$ is phenyl, pyridyl or thiophenyl, which are optionally substituted by up to 2 radicals independently of one another selected from the group of C$_1$-C$_4$-alkyl, fluorine, chlorine, trifluoromethyl, hydroxy, phenylcarbonylamino, C$_1$-C$_4$-alkyl-carbonylamino, C$_1$-C$_4$-alkylaminocarbonyl or phenylaminocarbonyl,
R$^1$ is phenyl or pyridyl, where phenyl is substituted by 1 to 2 radicals and pyridyl is optionally substituted by 1 to 2 radicals in each case independently of one another selected from the group of methyl, ethyl, 2-propyl, trifluoromethyl, methoxy, ethoxy, fluorine and chlorine,
or a salt thereof.

5. Process for preparing a compound according to claim 1, comprising:

[A] reacting a compound of the formula (II):

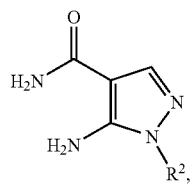

(II)

in which
R$^2$ has the meanings indicated in claim 1, with a compound of the formula (IIIa):

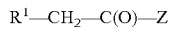

R$^1$—CH$_2$—C(O)—Z (IIIa), in which
R$^1$ has the meanings indicated in claim 1,
and
Z is chlorine or bromine, in an inert solvent and in the presence of a base, to provide a compound of the formula (IV):

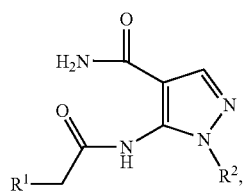

(IV)

in which
R$^1$ and R$^2$ have the meanings indicated in claim 1, and then cyclizing the compound of formula (IV) in an inert solvent in the presence of a base to provide a compound of the formula (I), or

[B] reacting a compound of the formula (II) with a compound of the formula (IIIb):

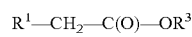

R$^1$—CH$_2$—C(O)—OR$^3$ (IIIb)

in which
R$^1$ has the meanings indicated in claim 1,
and
R$^3$ is methyl or ethyl,
in an inert solvent and in the presence of a base, with direct cyclization to a compound of formula (I), or

[C] reacting a compound of the formula (V):

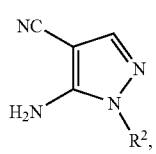

(V)

in which
R$^2$ has the meanings indicated in claim 1, with a compound of the formula (IIIa) in an inert solvent and in the presence of a base to provide a compound of the formula (V):

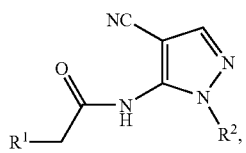

(VI)

in which
R$^1$ and R$^2$ have the meanings indicated in claim 1, and cyclizing the latter in a second step in an inert solvent and in the presence of a base and of an oxidizing agent to a compound of formula (I), and the resulting compounds of the formula (I) are, where a salt is prepared, reacted with the appropriate bases or acids to give the salt.

6. A pharmaceutical composition comprising at least one of the compounds of any one of claims 1 to 4 and at least one pharmaceutically acceptable, essentially non-toxic carrier or excipient.

* * * * *